US012577539B2

(12) United States Patent
Schaffer et al.

(10) Patent No.: US 12,577,539 B2
(45) Date of Patent: Mar. 17, 2026

(54) CELLS FOR ENHANCED PRODUCTION OF ADENO-ASSOCIATED VIRUS

(71) Applicant: The Regents of the University of California, Oakland, CA (US)

(72) Inventors: David V. Schaffer, Danville, CA (US); Christopher Barnes, Oakland, CA (US); David Stephen Ojala, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 1183 days.

(21) Appl. No.: 17/605,387

(22) PCT Filed: Apr. 22, 2020

(86) PCT No.: PCT/US2020/029316
§ 371 (c)(1),
(2) Date: Oct. 21, 2021

(87) PCT Pub. No.: WO2020/219543
PCT Pub. Date: Oct. 29, 2020

(65) Prior Publication Data
US 2022/0228129 A1 Jul. 21, 2022

Related U.S. Application Data

(60) Provisional application No. 62/839,375, filed on Apr. 26, 2019.

(51) Int. Cl.
| | |
|---|---|
| *C12N 7/00* | (2006.01) |
| *C12N 5/071* | (2010.01) |
| *C12N 9/22* | (2006.01) |
| *C12N 15/10* | (2006.01) |
| *C12N 15/11* | (2006.01) |
| *C12N 15/63* | (2006.01) |
| *C12N 15/85* | (2006.01) |
| *C12N 15/86* | (2006.01) |

(52) U.S. Cl.
CPC ............. *C12N 7/00* (2013.01); *C12N 5/0687* (2013.01); *C12N 9/22* (2013.01); *C12N 15/1058* (2013.01); *C12N 15/11* (2013.01); *C12N 15/63* (2013.01); *C12N 15/85* (2013.01); *C12N 15/86* (2013.01); *C12N*

*2310/20* (2017.05); *C12N 2510/02* (2013.01); *C12N 2750/14142* (2013.01); *C12N 2750/14152* (2013.01); *C12N 2800/107* (2013.01); *C12N 2800/80* (2013.01); *C12N 2840/002* (2013.01)

(58) Field of Classification Search
CPC ...... C12N 7/00; C12N 15/1058; C12N 15/11; C12N 15/63; C12N 15/85; C12N 15/86; C12N 2310/20; C12N 2310/02; C12N 2750/14152; C12N 2800/107
See application file for complete search history.

(56) References Cited

U.S. PATENT DOCUMENTS

| | | | |
|---|---|---|---|
| 2009/0215711 A1 | 8/2009 | Morris et al. | |
| 2016/0032317 A1 | 2/2016 | Rossi et al. | |
| 2016/0346359 A1 | 12/2016 | Buchlis et al. | |
| 2017/0029785 A1* | 2/2017 | Zhao ........................ | C12N 7/00 |
| 2018/0057810 A1 | 3/2018 | Zhang et al. | |

FOREIGN PATENT DOCUMENTS

| | | |
|---|---|---|
| WO | WO 2019/006418 | 1/2019 |
| WO | WO 2019/074907 | 4/2019 |

OTHER PUBLICATIONS

Rice, Lisa, et al. "Identification and functional analysis of SKA2 interaction with the glucocorticoid receptor." The Journal of endocrinology 198.3 (2008): 499. (Year: 2008).*

* cited by examiner

*Primary Examiner* — Kevin K Hill
*Assistant Examiner* — Allison Marie Johnson
(74) *Attorney, Agent, or Firm* — Schweta Chandra; Bozicevic, Field & Francis LLP

(57) ABSTRACT

The present disclosure provides an in vitro mammalian cell that is genetically modified to provide for enhanced production of adeno-associated virus (AAV) virions. The mammalian cells can be used to produce AAV virions, e.g., recombinant AAV virions that include a heterologous nucleic acid encoding a gene product; the present disclosure thus provides methods for producing an AAV virion, which may be a recombinant AAV virion.

10 Claims, 18 Drawing Sheets
Specification includes a Sequence Listing.

FIG. 1
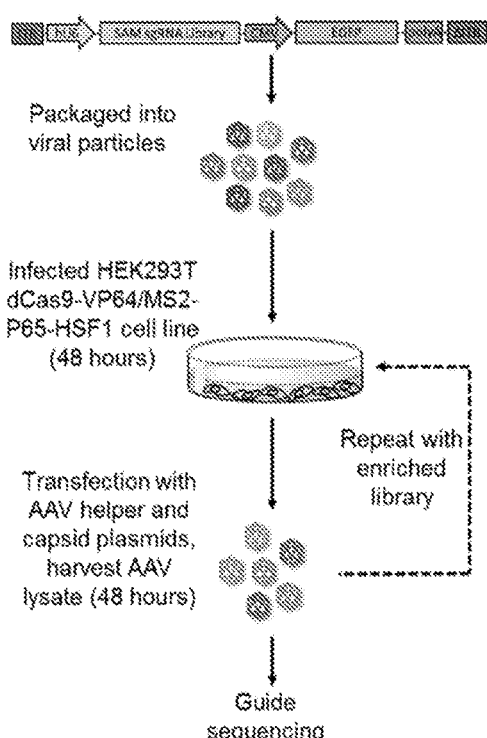
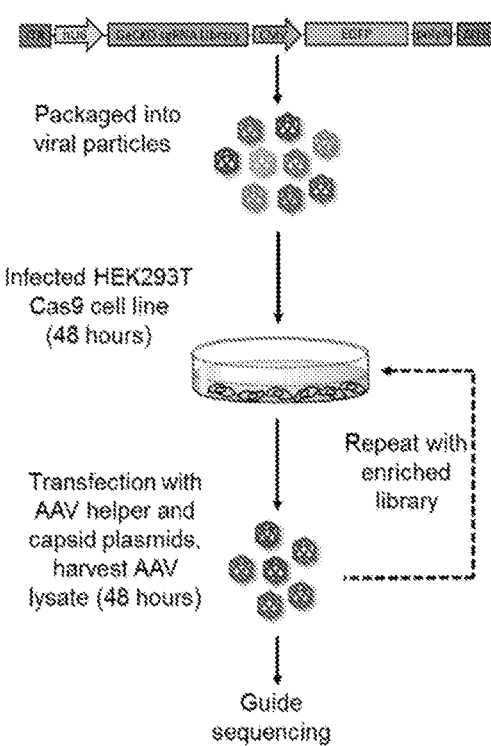

C

| Library | Guide RNA | Fold Increase |
|---------|-----------|---------------|
| GeCKO | G 5 – Endoplasmic reticulum lectin 1 | 2222 |
| SAM | S 1 – CUGBP, Elva-like family member 2(CELF2), transcript variant 3 | 1545 |
| | S 4 – Inositol 1,4,5-triphosphate receptor interacting protein (ITPRIP) transcript variant 2 | 2284 |
| | S 6 – Spindle and Kinetochore associated complex subunit 2 (SKA2) transcript variant 2 | 2690 |

D  Viral Titer Increase in gRNA Expressing Cell Line

FIG. 6

ITPRIP2 (GenBank XP_005270314 and NP_001258941)
*Homo sapiens* inositol 1,4,5-trisphosphate receptor-interacting protein isoform X1

```
MAMGLFRVCL   VVVTAIINHP   LLFPRENATV   PENEEEIIRK   MQAHQEKLQL   EQLRLEEEVA

RLAAEKEALE   QVAEEGRQQN   ETRVTWDLWS   TLCMILFLMI   EVWRQDHQEG   PSPECLGGEE

DELPGLGGAP   LQGLTLPNKA   TLGHFYERCI   RGATADAART   REFLEGFVDD   LLEALRSLCN

RDTDMEVEDF   IGVDSMYENW   QVDRPLLCHL   FVPFTPPEPY   RFHPELWCSG   RSVPLDRQGY

GQIKVVRADG   DTLSCICGKT   KLGEDMLCLL   HGRNSMAPPC   GDMENLLCAT   DSLYLDTMQV

MKWFQTALTR   AWKGIAHKYE   FDLAFGQLDS   PGSLKIKFRS   GKFMPFNLIP   VIQCDDSDLY

FVSHLPREPS   EGTPASSTDW   LLSFAVYERH   FLRTTLKALP   EGACHLSCLQ   IASFLLSKQS

RLTGPSGLSS   YHLKTALLHL   LLLRQAADWK   AGQLDARLHE   LLCFLEKSLL   QKKLHHFFIG

NRKVPEAMGL   PEAVLRAEPL   NLFRPFVLQR   SLYRKTLDSF   YEMLKNAPAL   ISEYSLHVPS

DQPTPKS (SEQ ID NO://)
```

FIG. 7

*Homo sapiens* CUGBP Elav-like family member 2 (CELF2) isoform 3
GenBank NP_001313261 and NP_001020248

```
  1 MRCPKSAVTM RNEELLLSNG TANKMNGALD HSDQPDPDAI KMFVGQIPRS WSEKELKELF
 61 EPYGAVYQIN VLRDRSQNPP QSKGCCFVTF YTRKAALEAQ NALHNIKTLP GMHHPIQMKP
121 ADSEKSNAVE DRKLFIGMVS KKCNENDIRV MFSPFGQIEE CRILRGPDGL SRGCAFVTFS
181 TRAMAQNAIK AMHQSQTMEG CSSPIVVKFA DTQKDKEQRR LQQQLAQQMQ QLNTATWGNL
241 TGLGGLTPQY LALLQQATSS SNLGAFSGIQ QMAGMNALQL QNLATLAAAA AAAQTSATST
301 NANPLSTTSS ALGALTSPVA ASTPNSTAGA AMNSLTSLGT LQGLAGATVG LNNINALAGM
361 AALNGGLGAT GLTNGTAGTM DALTQAYSGI QQYAAAALPT LYSQSLLQQQ SAAGSQKEGP
421 EGANLFIYHL PQEFGDQDIL QMFMPFGNVI SAKVFIDKQT NLSKCFGFVS YDNPVSAQAA
481 IQAMNGFQIG MKRLKVQLKR SKNDSKPY
```

FIG. 8

*Homo sapiens* centrosomal protein of 128 kDa (CEP128)
GenBank NP_689659

```
   1 MAESSSESDH FRCRDRLSPW AARSTHRGTR SLPTVEVTEK VNTITSTLQD TSRNLRQVDQ
  61 MLGRYREYSN GQAGAIEHLK ESLEQSIDQL RSQRLLRNSG GRSISVTSLS ASDLDGGTGS
 121 ELHHFPPTSP LKDYGDPQGI KRMRSRTGVR FVQETDDMTQ LHGFHQSLRD LSSEQIRLGD
 181 DFNRELSRRS RSDAETKRAL EELTEKLNEA QKQEVVSDRV ERRLQELERE MRTERELVER
 241 RQDQLGLMSL QLQEALKKQE AKADEHEGAI KNKLRQTETE KNQLEQELEL SRRLLNQSEG
 301 SRETLLHQVE ELRTQLTKAE GDRKGLQHQV SQISKQQSNY QDEQGEDWRF RRGVEREKQD
 361 LEKQMSDLRV QLNFSAMASE LEEVKRCMER KDKEKAHLAS QVENLTRELE NGEKQQLQML
 421 DRLKEIQNHF DTCEAERKHA DLQISELTRH AEDATKQAER YLSELQQSEA LKEEAEKRRE
 481 DLKLKAQESI RQWKLKHKKL ERALEKQSET VDELTGKNNQ ILKEKDELKT QLYAALQQIE
 541 NLRKELNDVL TKRALQEEEL HSKEEKLRDI KSHQADLELE VKNSLDTIHR LESELKKQSK
 601 IQSQMKVEKA HLEEEIAELK KSQAQDKAKL LEMQESIKDL SAIRADLANK LAEEERAKKA
 661 VLKDLSDLTA QAKSRDEETA TIITQLKLER DVHQRELKDL TSSLQSVKTK HEQNIQELMK
 721 HFKKEKSEAE NHIRTLKAES LEEKNMAKIH RGQLEKLKSQ CDRLTEELTQ NENENKKLKL
 781 KYQCLKDQLE EREKHISIEE EHLRRMEEAR LQLKDQLLCL ETEQESILGV IGKEIDAACK
 841 TFSKDSVEKL KVFSSGPDIH YDPHRWLAES KTKLQWLCEE LKERENREKN LRHQLMLCRQ
 901 QLRNLTENKE SELQCLFQQI ERQEQLLDEI HREKRDLLEE TQRKDEEMGS LQDRVIALET
 961 STQVALDHLE SVPEKLSLLE DFKDFRDSCS SSERTDGRYS KYRVRRNSLQ HHQDDTKYRT
1021 KSFKGDRTFL EGSHTRGLDH SSSWQDHSRF LSSPRFSYVN SFTKRTVAPD SASNKEDATM
1081 NGTSSQPKKE EYGS
```

FIG. 9

*Homo sapiens* protocadherin alpha-2 (PCDHA2) isoform 1
GenBank NP_061728

```
  1 MASSIRRGRG AWTRLLSLLL LAAWEVGSGQ LRYSVPEEAK HGTFVGRIAQ DLGLELEELV
 61 PRLFRVASKR HGDLLEVNLQ NGILFVNSRI DREELCGRSA ECSIHVEVIV DRPLQVFHVE
121 VEVKDINDNP PIFPMTVKTI RFPESRLLDS RFPLEGASDA DIGVNALLSY KLSSSEFFFL
181 DIQANDELSE SLSLVLGKSL DREETAEVNL LLVATDGGKP ELTGTVQILI KVLDVNDNEP
241 TFAQSVYKVK LLENTANGTL VVKLNASDAD EGPNSEIVYS LGSDVSSTIQ TKFTIDPISG
301 EIRTKGKLDY EEAKSYEIQV TATDKGTPSM SGHCKISLKL VDINDNTPEV SITSLSLPIS
361 ENASLGTVIA LITVSDRDSG TNGHVTCSLT PHVPFKLVST FKNYYSLVLD SALDRESVSA
421 YELVVTARDG GSPSLWATTS VSIEVADVND NAPAFAQPEY TVFVKENNPP GCHIFTVSAW
481 DADAQENALV SYSLVERRVG ERALSSYVSV HAESGKVYAL QPLDHEEVEL LQFQVSARDA
541 GVPPLGSNVT LQVFVLDEND NAPALLAPRA GTAAGAVSEL VPWSVGAGHV VAKVRAVDAD
601 SGYNAWLSYE LQLGTGSARI PFRVGLYTGE ISTTRALDEA DSPRHRLLVL VKDHGEPALT
661 ATATVLVSLV ESGQAPKASS RAWVGAAGSE ATLVDVNVYL IIAICAVSSL LVLTVLLYTA
721 LRCSVPPTEG ARAPGKPTLV CSSAVGSWSY SQQRRQRVCS GEDPPKTDLM AFSPSLSQGP
781 DSAEEKQLSE SEYVGKPRQP NPDWRYSASL RAGMHSSVHL EEAGILRAGP GGPDQQWPTV
841 SSATPEPEAG EVSPPVGAGV NSNSWTFKYG PGNPKQSGPG ELPDKFIIPG SPAIISIRQE
901 PTNSQIDKSD FITFGKKEET KKKKKKKGN KTQEKKEKGN STTDNSDQ
```

FIG. 10

*Homo sapiens* acetylcholinesterase (Cartwright blood group) (ACHE), isoform E4-E6
GenBank NP_000656

```
  1 MRPPQCLLHT PSLASPLLLL LLWLLGGGVG AEGREDAELL VTVRGGRLRG IRLKTPGGPV
 61 SAFLGIPFAE PPMGPRRFLP PEPKQPWSGV VDATTFQSVC YQYVDTLYPG FEGTEMWNPN
121 RELSEDCLYL NVWTPYPRPT SPTPVLVWIY GGGFYSGASS LDVYDGRFLV QAERTVLVSM
181 NYRVGAFGFL ALPGSREAPG NVGLLDQRLA LQWVQENVAA FGGDPTSVTL FGESAGAASV
241 GMHLLSPPSR GLFHRAVLQS GAPNGPWATV GMGEARRRAT QLAHLVGCPP GGTGGNDTEL
301 VACLRTRPAQ VLVNHEWHVL PQESVFRFSF VPVVDGDFLS DTPEALINAG DFHGLQVLVG
361 VVKDEGSYFL VYGAPGFSKD NESLISRAEF LAGVRVGVPQ VSDLAAEAVV LHYTDWLHPE
421 DPARLREALS DVVGDHNVVC PVAQLAGRLA AQGARVYAYV FEHRASTLSW PLWMGVPHGY
481 EIEFIFGIPL DPSRNYTAEE KIFAQRLMRY WANFARTGDP NEPRDPKAPQ WPPYTAGAQQ
541 YVSLDLRPLE VRRGLRAQAC AFWNRFLPKL LSATDTLDEA ERQWKAEFHR WSSYMVHWKN
601 QFDHYSKQDR CSDL
```

FIG. 11

*Homo sapiens* endoplasmic reticulum lectin 1 (ERLEC1)
GenBank NP_056516

```
  1 MEEGGGGVRS LVPGGPVLLV LCGLLEASGG GRALPQLSDD IPFRVNWPGT EFSLPTTGVL
 61 YKEDNYVIMT TAHKEKYKCI LPLVTSGDEE EEKDYKGPNP RELLEPLFKQ SSCSYRIESY
121 WTYEVCHGKH IRQYHEEKET GQKINIHEYY LGNMLAKNLL FEKEREAEEK EKSNEIPTKN
181 IEGQMTPYYP VGMGNGTPCS LKQNRPRSST VMYICHPESK HEILSVAEVT TCEYEVVILT
241 PLLCSHPKYR FRASPVNDIF CQSLPGSPFK PLTLRQLEQQ EEILRVPFRR NKEEDLQSTK
301 EERFPAIHKS IAIGSQPVLT VGTTHISKLT DDQLIKEFLS GSYCFRGGVG WWKYEFCYGK
361 HVHQYHEDKD SGKTSVVVGT WNQEEHIEWA KKNTARAYHL QDDGTQTVRM VSHFYGNGDI
421 CDITDKPRQV TVKLKCKESD SPHAVTVYML EPHSCQYILG VESPVICKIL DTADENGLLS
481 LPN
```

FIG. 12

*Homo sapiens* kinesin-like protein (KIF23), isoform 1
GenBank NP_612565

```
  1 MKSARAKTPR KPTVKKGSQT NLKDPVGVYC RVRPLGFPDQ ECCIEVINNT TVQLHTPEGY
 61 RLNRNGDYKE TQYSFKQVFG THTTQKELFD VVANPLVNDL IHGKNGLLFT YGVTGSGKTH
121 TMTGSPGEGG LLPRCLDMIF NSIGSFQAKR YVFKSNDRNS MDIQCEVDAL LERQKREAMP
181 NPKTSSSKRQ VDPEFADMIT VQEFCKAEEV DEDSVYGVFV SYIEIYNNYI YDLLEEVPFD
241 PIKPKPPQSK LLREDKNHNM YVAGCTEVEV KSTEEAFEVF WRGQKKRRIA NTHLNRESSR
301 SHSVFNIKLV QAPLDADGDN VLQEKEQITI SQLSLVDLAG SERTNRTRAE GNRLREAGNI
361 NQSLMTLRTC MDVLRENQMY GTNKMVPYRD SKLTHLFKNY FDGEGKVRMI VCVNPKAEDY
421 EENLQVMRFA EVTQEVEVAR PVDKAICGLT PGRRYRNQPR GPVGNEPLVT DVVLQSFPPL
481 PSCEILDIND EQTLPRLIEA LEKRHNLRQM MIDEFNKQSN AFKALLQEFD NAVLSKENHM
541 QGKLNEKEKM ISGQKLEIER LEKKNKTLEY KIEILEKTTT IYEEDKRNLQ QELETQNQKL
601 QRQFSDKRRL EARLQGMVTE TTMKWEKECE RRVAAKQLEM QNKLWVKDEK LKQLKAIVTE
661 PKTEKPERPS RERDREKVTQ RSVSPSPVPL SSNYIAQISN GQQLMSQPQL HRRSNSCSSI
721 SVASCISEWE QKIPTYNTPL KVTSIARRRQ QEPGQSKTCI VSDRRRGMYW TEGREVVPTF
781 RNEIEIEEDH CGRLLFQPDQ NAPPIRLRHR RSRSAGDRWV DHKPASNMQT ETVMQPHVPH
841 AITVSVANEK ALAKCEKYML THQELASDGE IETKLIKGDI YKTRGGGQSV QFTDIETLKQ
901 ESPNGSRKRR SSTVAPAQPD GAESEWTDVE TRCSVAVEMR AGSQLGPGYQ HHAQPKRKKP
```

FIG. 13

*Homo sapiens* interferon-induced protein with tetratricopeptide repeats 5 (IFIT5)
GenBank NP_036552

```
  1 MSEIRKDTLK AILLELECHF TWNLLKEDID LFEVEDTIGQ QLEFLTTKSR LALYNLLAYV
 61 KHLKGQNKDA LECLEQAEEI IQQEHSDKEE VRSLVTWGNY AWVYYHMDQL EEAQKYTGKI
121 GNVCKKLSSP SNYKLECPET DCEKGWALLK FGGKYYQKAK AAFEKALEVE PDNPEFNIGY
181 AITVYRLDDS DREGSVKSFS LGPLRKAVTL NPDNSYIKVF LALKLQDVHA EAEGEKYIEE
241 ILDQISSQPY VLRYAAKFYR RKNSWNKALE LLKKALEVTP TSSFLHHQMG LCYRAQMIQI
301 KKATHNRPKG KDKLKVDELI SSAIFHFKAA MERDSMFAFA YTDLANMYAE GGQYSNAEDI
361 FRKALRLENI TDDHKHQIHY HYGRFQEFHR KSENTAIHHY LEALKVKDRS PLRTKLTSAL
421 KKLSTKRLCH NALDVQSLSA LGFVYKLEGE KRQAAEYYEK AQKIDPENAE FLTALCELRL
481 SI
```

FIG. 14

*Homo sapiens* caspase recruitment domain-containing protein 8 (CARD8), isoform a
GenBank NP_001338711

```
  1 MEKKECPEKS SSSEEELPRR DSGSSRNIDA SKLIRLQGSR KLLVDNSIRE LQYTKTGIFF
 61 QAEACVTNDT VYRELPCVSE TLCDISHFFQ EDDETEAEPL LFRAVPECQL SGGDIPSVSE
121 EQESSEGQDS GDICSEENQI VSSYASKVCF EIEEDYKNRQ FLGPEGNVDV ELIDKSTNRY
181 SVWFPTAGWY LWSATGLGFL VRDEVTVTIA FGSWSQHLAL DLQHHEQWLV GGPLFDVTAE
241 PEEAVAEIHL PHFISLQAGE VDVSWFLVAH FKNEGMVLEH PARVEPFYAV LESPSFSLMG
301 ILLRIASGTR LSIPITSNTL IYYHPHPEDI KFHLYLVPSD ALLTKAIDDE EDRFHGVRLQ
361 TSPPMEPLNF GSSYIVSNSA NLKVMPKELK LSYRSPGEIQ HFSKFYAGQM KEPIQLEITE
421 KRHGTLVWDT EVKPVDLQLV AASAPPPFSG AAFVKENHRQ LQARMGDLKG VLDDLQDNEV
481 LTENEKELVE QEKTRQSKNE ALLSMVEKKG DLALDVLFRS ISERDPYLVS YLRQQNL
```

FIG. 15

*Homo sapiens* chromosome 5 open reading frame 52 (C5orf52)
GenBank NP_001138604

```
  1 MTQPTRPSVT CDQGSSTIGG TAAQATTSSS ATSGSNYQRD RLGRRPEIGV GGQPQICFPR
 61 PRSAQQPVLF SLMNSSEAAM KKTLPKSHLS RVIIHDNRIT QRIYEMEVSA LEKTKKKISH
121 YYEHLKKKFM TEQLRKLGRW REESVNSNRY LTFGIPPPV
```

FIG. 16
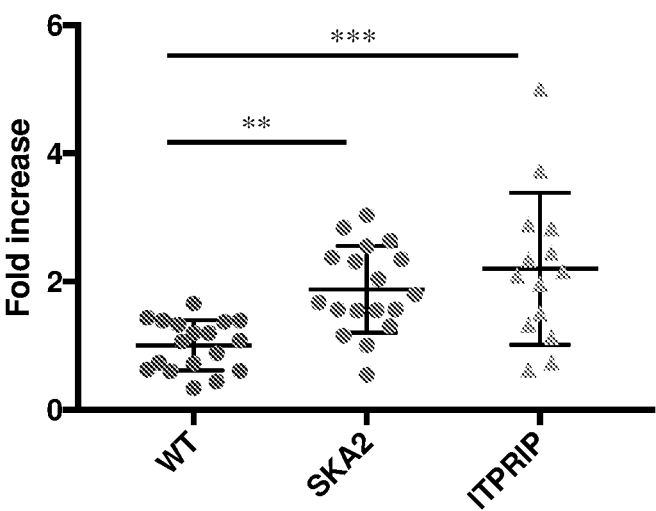
AAV2 viral fold increase
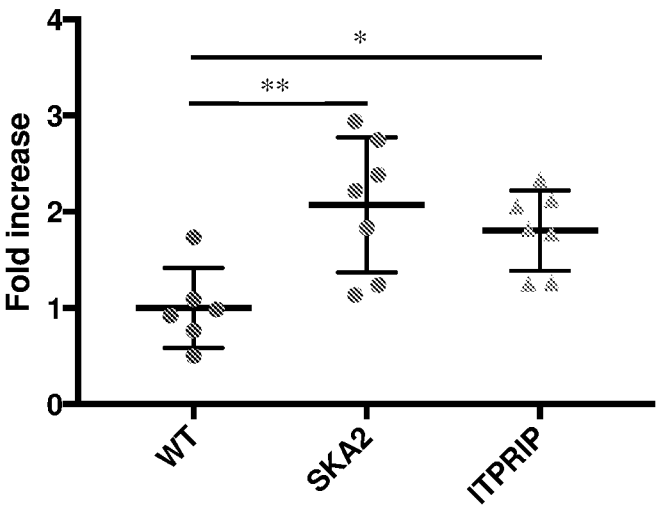
AAV6 viral fold increase

FIG. 17
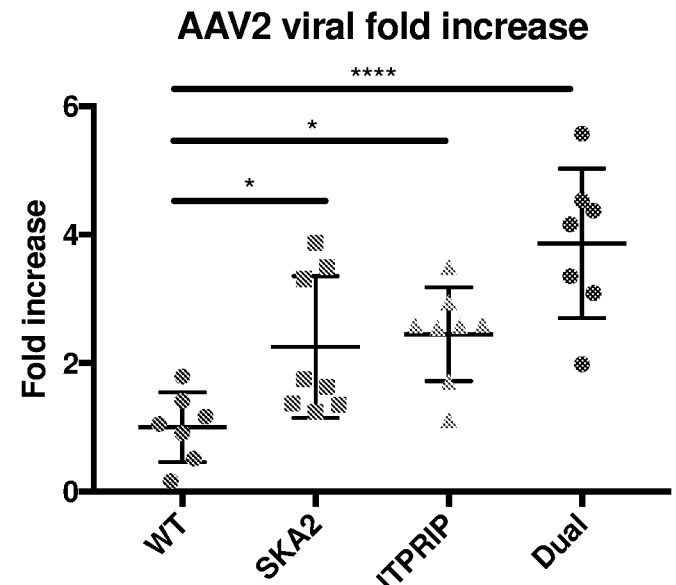
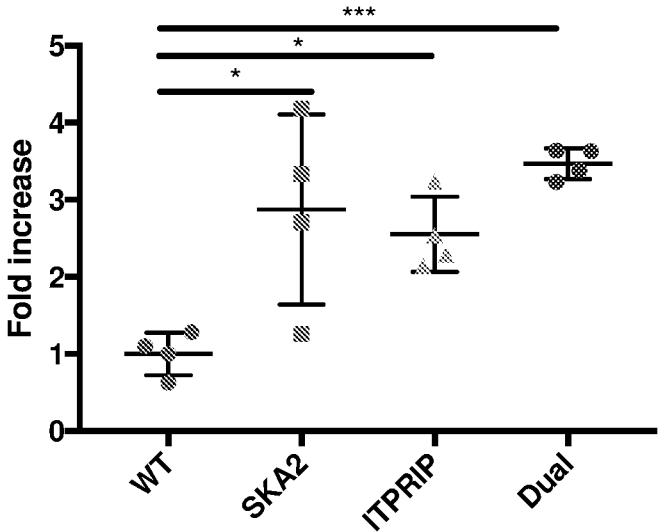

FIG. 19 (Table 1)

| AAV2 | Sample | Titer | Average | Fold Increase |
|---|---|---|---|---|
| | | *ss vg/ 15 cm plate* | | |
| 4-18-19 titering | WT | 4.0677E+10 | 7.02E+10 | 1.00E+00 |
| | WT | 1.1235E+11 | | |
| | WT | 7.1891E+10 | | |
| | WT | 9.289E+10 | | |
| 9-9-19 titering | WT | 7.03E+09 | | |
| | WT | 4.53E+10 | | |
| | WT | 8.66E+10 | | |
| | WT | 1.05E+11 | | |
| 4-18-19 titering | SKA2 | 1.2932E+11 | 1.45687E+11 | 2.08E+00 |
| | SKA2 | 2.7767E+11 | | |
| | SKA2 | 2.0457E+11 | | |
| | SKA2 | 3.0713E+11 | | |
| 9-9-19 titering | SKA2 | 5.3388E+10 | | |
| | SKA2 | 7.5747E+10 | | |
| | SKA2 | 5.8477E+10 | | |
| | SKA2 | 5.92E+10 | | |
| 4-18-19 titering | ITPRIP | 2.0685E+11 | 1.50397E+11 | 2.14E+00 |
| | ITPRIP | 2.347E+11 | | |
| | ITPRIP | 1.3617E+11 | | |
| | ITPRIP | 2.0551E+11 | | |
| 9-9-19 titering | ITPRIP | 1.0999E+11 | | |
| | ITPRIP | 1.1145E+11 | | |
| | ITPRIP | 4.8001E+10 | | |
| | ITPRIP | 1.5049E+11 | | |
| 4-18-19 titering | Dual | 1.5726E+11 | 2.69087E+11 | 3.83E+00 |
| | Dual | 3.4724E+11 | | |
| | Dual | 2.6591E+11 | | |
| | Dual | 4.4288E+11 | | |
| 9-9-19 titering | Dual | 1.7944E+11 | | |
| | Dual | 4.3086E+11 | | |
| | Dual | 1.3354E+11 | | |
| | Dual | 1.9556E+11 | | |

FIG. 20 (Table 2)

| AAV6 | Sample | Titer | Average | Fold Increase |
|---|---|---|---|---|
| | | ss vg/ 15 cm plate | | |
| 3-27-19 titering | WT | 7.00E+10 | 5.48E+10 | 1.00 |
| | WT | 6.02E+10 | | |
| | WT | 3.43E+10 | | |
| 3-27-19 titering | SKA2 | 6.92E+10 | 1.58E+11 | 2.87 |
| | SKA2 | 1.83E+11 | | |
| | SKA2 | 1.48E+11 | | |
| | SKA2 | 2.29E+11 | | |
| 3-27-19 titering | ITPRIP | 1.17E+11 | 1.40E+11 | 2.55 |
| | ITPRIP | 1.25E+11 | | |
| | ITPRIP | 1.77E+11 | | |
| | ITPRIP | 1.39E+11 | | |
| 3-27-19 titering | Dual | 1.85E+11 | 1.90E+11 | 3.47 |
| | Dual | 1.77E+11 | | |
| | Dual | 1.99E+11 | | |
| | Dual | 2.00E+11 | | |

CELLS FOR ENHANCED PRODUCTION OF ADENO-ASSOCIATED VIRUS

CROSS-REFERENCE

This application is a national phase filing of PCT/US2020/029316, filed Apr. 22, 2020, which application claims the benefit of U.S. Provisional Patent Application No. 62/839,375, filed Apr. 26, 2019, which applications are incorporated herein by reference in their entirety.

STATEMENT REGARDING FEDERALLY SPONSORED RESEARCH

This invention was made with government support under Grant No. EB021572 awarded by the National Institutes of Health. The government has certain rights in the invention.

INCORPORATION BY REFERENCE OF SEQUENCE LISTING PROVIDED AS A TEXT FILE

A Sequence Listing is provided as a text file, "BERK-408WO_SeqListing_ST25" created on Mar. 31, 2020 and having a size of 55,844 bytes. The contents of the text file are incorporated by reference herein in their entirety.

INTRODUCTION

Gene therapy is a therapeutic modality that involves the delivery of DNA to a cell to treat genetic disease. Common delivery technologies include viral vectors, lipid delivery, and naked-DNA delivery, and while the latter two technologies boast low immune profiles, repeat administration ability, and lack of transgene size limit, the technologies are highly inefficient in vivo. Viral vectors are far more efficient and include a number of properties that make them advantageous. A currently used viral vector for in vivo delivery is Adeno-Associated Virus (AAV). AAV is exhibits low immunogenicity and low random integration rate, making it one of the safest DNA delivery methods. Current AAV-mediated gene therapy is challenged by limitations in manufacturing sufficient quantities to satisfy demand.

There is a need in the field for cell lines that produce AAV in higher quantities than currently available using, e.g., human embryonic kidney (HEK) cells.

SUMMARY

The present disclosure provides an in vitro mammalian cell that is genetically modified to provide for enhanced production of adeno-associated virus (AAV) virions. The mammalian cells can be used to produce AAV virions, e.g., recombinant AAV virions that include a heterologous nucleic acid encoding a gene product; the present disclosure thus provides methods for producing an AAV virion, which may be a recombinant AAV virion.

BRIEF DESCRIPTION OF THE DRAWINGS

FIG. 1 presents schematic depictions of an iterative AAV manufacturing enhancement process through genetic manipulation via either over-expression mediated by dCas9-VP64 (left panel) or genetic knock-out via Cas9 (right panel).

FIG. 6 provides an amino acid sequence of an inositol 1,4,5-trisphosphate receptor-interacting protein (ITPRIP) isoform X1. The sequence is set forth in SEQ ID NO: 3.

FIG. 7 provides an amino acid sequence of a CUGBP Elav-like family member 2 (CELF2), isoform 3, polypeptide. The sequence is set forth in SEQ ID NO: 4.

FIG. 8 provides an amino acid sequence of a centrosomal protein of 128 kDa (CEP128) polypeptide. The sequence is set forth in SEQ ID NO: 5.

FIG. 9 provides an amino acid sequence of a protocadherin alpha-2 (PCDHA2), isoform 1, polypeptide. The sequence is set forth in SEQ ID NO: 6.

FIG. 10 provides an amino acid sequence of an acetylcholinesterase (Cartwright blood group) (ACHE), isoform E4-E6, polypeptide. The sequence is set forth in SEQ ID NO: 7.

FIG. 11 provides an amino acid sequence of an endoplasmic reticulum lectin 1, isoform 1, polypeptide. The sequence is set forth in SEQ ID NO: 8.

FIG. 12 provides an amino acid sequence of a kinesin-like protein (KIF23), isoform 1, polypeptide. The sequence is set forth in SEQ ID NO: 9.

FIG. 13 provides an amino acid sequence of an interferon-induced protein with tetratricopeptide repeats 5 (IFIT5) polypeptide. The sequence is set forth in SEQ ID NO: 10.

FIG. 14 provides an amino acid sequence of a caspase recruitment domain-containing protein 8 (CARD8) polypeptide. The sequence is set forth in SEQ ID NO: 11.

FIG. 15 provides an amino acid sequence of a chromosome 5 open reading frame 52 (C5orf52) polypeptide. The sequence is set forth in SEQ ID NO: 12.

FIG. 16 depicts increase AAV2 (upper panel) and AAV6 (lower panel) in the number of viral genomes with each round, normalized to the wild-type (WT) 293 Ts value for that round, from SKA2- and ITPRIP-expressing cells.

FIG. 17 depicts increase AAV2 (upper panel) and AAV6 (lower panel) in the number of viral genomes with each round, normalized to the WT 293 Ts value for that round.

FIG. 19 presents Table 1: Compiled AAV2 viral titers from WT 293 Ts as well as 293 Ts induced to express: i) SKA2; ii) ITPRIP; or iii) both SKA2 and ITPRIP simultaneously ("dual")

FIG. 20 presents Table 2: Compiled AAV6 viral titers from WT 293 Ts as well as 293 Ts induced to express: i) SKA2; ii) ITPRIP; or iii) both SKA2 and ITPRIP simultaneously ("dual").

DEFINITIONS

Figure 2A:
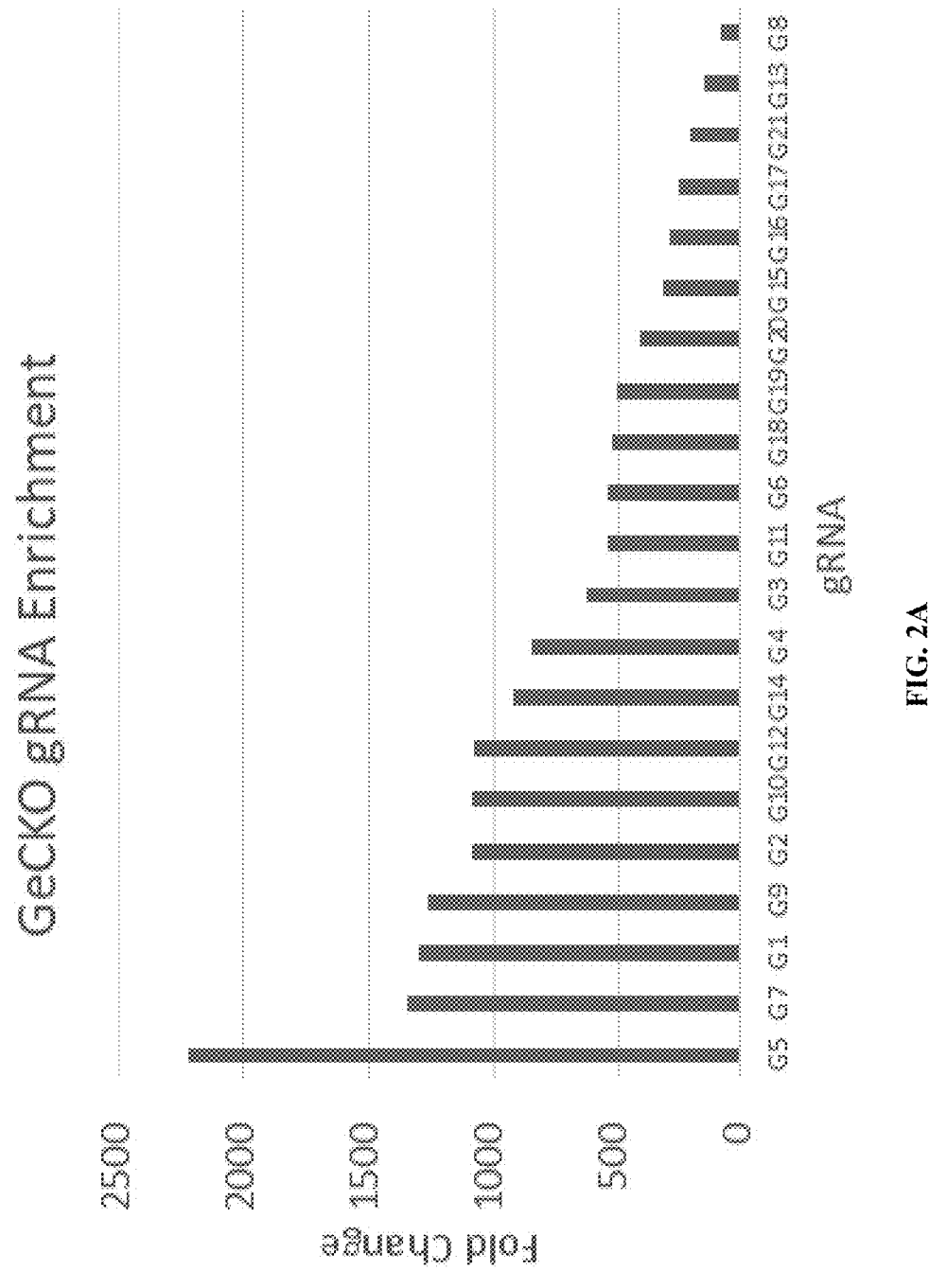
FIG. 2A-2D depict: A) the top hits from the GeCKO selection ranked in descending order; B) the top hits from the SAM selection ranked in descending order; C) fold increase of hits increased by over 1500-fold and the corresponding gene; D) quantification of vg/mL and fold increase over AAV2 production in wildtype HEK293 Ts of cells constitutively expressing the guide RNA linked to increased AAV manufacturing capability.
Figure 2B:
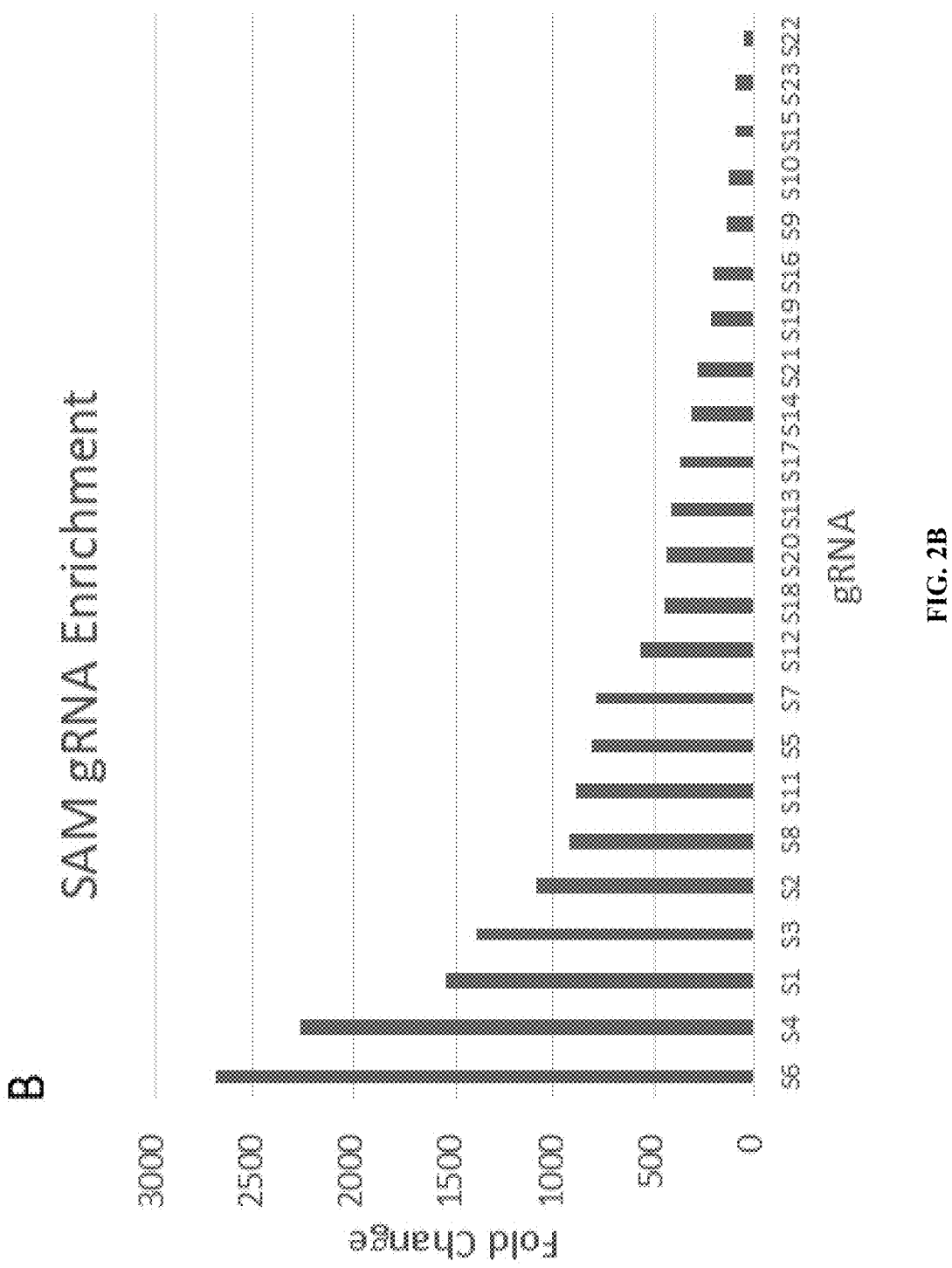
Figures 2C, 2D:
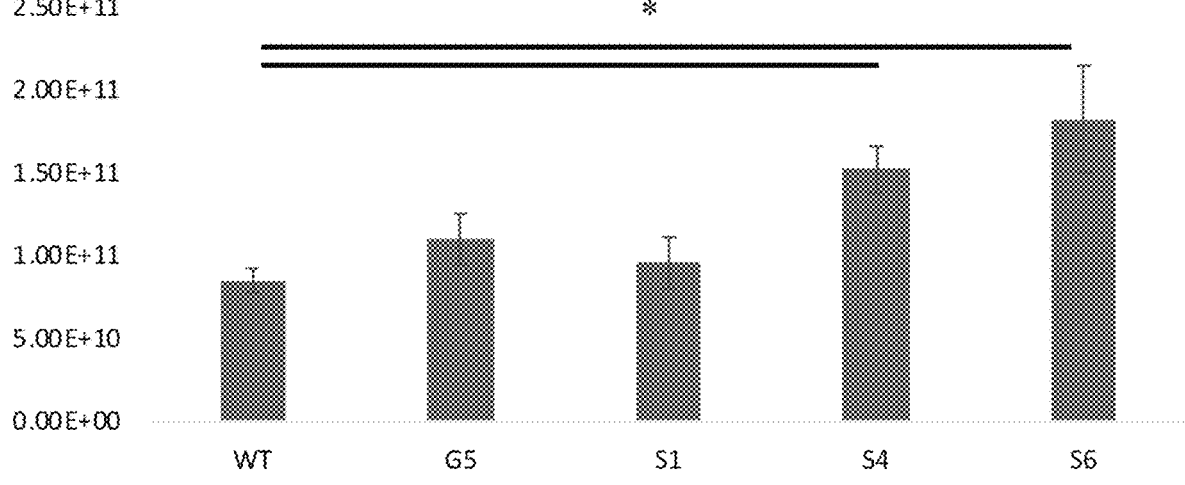

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), AAV type 10 (AAV-10), AAV type 11 (AAV-11), avian AAV, bovine AAV, canine AAV, equine AAV, primate AAV, non-primate AAV, and ovine AAV. See, e.g., Mori et al. (2004) *Virology* 330:375. The term "AAV" also includes chimeric AAV. "Primate AAV" refers to AAV isolated from a primate, "non-primate AAV" refers to AAV isolated from a non-primate mammal, "bovine AAV" refers to AAV isolated from a bovine mammal (e.g., a cow), etc.

An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two AAV inverted terminal repeat sequences (ITRs). The term rAAV vector encompasses both rAAV vector particles and rAAV vector plasmids.

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome, such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

"Packaging" refers to a series of intracellular events that result in the assembly and encapsidation of an AAV particle.

AAV "rep" and "cap" genes refer to polynucleotide sequences encoding replication and encapsidation proteins of adeno-associated virus. AAV rep and cap are referred to herein as AAV "packaging genes."

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans.

An "infectious" virus or viral particle is one that comprises a polynucleotide component which it is capable of delivering into a cell for which the viral species is tropic. The term does not necessarily imply any replication capacity of the virus. As used herein, an "infectious" virus or viral particle is one that can access a target cell, can infect a target cell, and can express a heterologous nucleic acid in a target cell. Thus, "infectivity" refers to the ability of a viral particle to access a target cell, infect a target cell, and express a heterologous nucleic acid in a target cell. Infectivity can refer to in vitro infectivity or in vivo infectivity. Assays for counting infectious viral particles are described elsewhere in this disclosure and in the art. Viral infectivity can be expressed as the ratio of infectious viral particles to total viral particles. Total viral particles can be expressed as the number of viral genome (vg) copies. The ability of a viral particle to express a heterologous nucleic acid in a cell can be referred to as "transduction." The ability of a viral particle to express a heterologous nucleic acid in a cell can be assayed using a number of techniques, including assessment of a marker gene, such as a green fluorescent protein (GFP) assay (e.g., where the virus comprises a nucleotide sequence encoding GFP), where GFP is produced in a cell infected with the viral particle and is detected and/or measured; or the measurement of a produced protein, for example by an enzyme-linked immunosorbent assay (ELISA). Viral infectivity can be expressed as the ratio of infectious viral particles to total viral particles. Methods of determining the ratio of infectious viral particle to total viral particle are known in the art. See, e.g., Grainger et al. (2005) *Mol. Ther.* 11:S337 (describing a TCID50 infectious titer assay); and Zolotukhin et al. (1999) *Gene Ther.* 6:973.

A "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per $10^2$ rAAV particles, less than about 1 rcAAV per $10^4$ rAAV particles, less than about 1 rcAAV per $10^8$ rAAV particles, less than about 1 rcAAV per $10^{12}$ rAAV particles, or no rcAAV).

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double-and single-stranded molecules. Unless otherwise specified or required, any embodiment of the invention described herein that is a polynucleotide encompasses both the double-stranded form and each of two complementary single-stranded forms known or predicted to make up the double-stranded form.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wisconsin, USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, California, USA. Alignment programs that permit gaps in the sequence can be used. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J Mol. Biol.* 48: 443-453 (1970).

Of interest is the BestFit program using the local homology algorithm of Smith Waterman (Advances in Applied Mathematics 2: 482-489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wisconsin, USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters:

Mismatch Penalty: 1.00;
Gap Penalty: 1.00;
Gap Size Penalty: 0.33; and
Joining Penalty: 30.0.

A "gene" refers to a polynucleotide containing at least one open reading frame that is capable of encoding a particular protein after being transcribed and translated.

The term "guide RNA", as used herein, refers to an RNA that comprises: i) an "activator" nucleotide sequence that binds to a CRISPR/Cas effector polypeptide (e.g., a class 2 CRISPR/Cas effector polypeptide such as a type II, type V, or type VI CRISPR/Cas effector polypeptide) and activates the CRISPR/Cas effector polypeptide; and ii) a "targeter" nucleotide sequence that comprises a nucleotide sequence that hybridizes with a target nucleic acid. The "activator"

nucleotide sequence and the "targeter" nucleotide sequence can be on separate RNA molecules (e.g., a "dual-guide RNA"); or can be on the same RNA molecule (a "single-guide RNA").

A "small interfering" or "short interfering RNA" or siRNA is a RNA duplex of nucleotides that is targeted to a gene interest (a "target gene"). An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

As used herein, the term "microRNA" refers to any type of interfering RNAs, including but not limited to, endogenous microRNAs and artificial microRNAs (e.g., synthetic miRNAs). Endogenous microRNAs are small RNAs naturally encoded in the genome which are capable of modulating the productive utilization of mRNA. An artificial microRNA can be any type of RNA sequence, other than endogenous microRNA, which is capable of modulating the activity of an mRNA. A microRNA sequence can be an RNA molecule composed of any one or more of these sequences. MicroRNA (or "miRNA") sequences have been described in publications such as Lim, et al., 2003, Genes & Development, 17, 991-1008, Lim et al., 2003, Science, 299, 1540, Lee and Ambrose, 2001, Science, 294, 862, Lau et al., 2001, Science 294, 858-861, Lagos-Quintana et al., 2002, Current Biology, 12, 735-739, Lagos-Quintana et al., 2001, Science, 294, 853-857, and Lagos-Quintana et al., 2003, *RNA*, 9, 175-179. Examples of microRNAs include any RNA that is a fragment of a larger RNA or is a miRNA, siRNA, stRNA, sncRNA, tncRNA, snoRNA, smRNA, shRNA, snRNA, or other small non-coding RNA. See, e.g., US Patent Applications 20050272923, 20050266552, 20050142581, and 20050075492. A "microRNA precursor" (or "pre-miRNA") refers to a nucleic acid having a stem-loop structure with a microRNA sequence incorporated therein. A "mature microRNA" (or "mature miRNA") includes a microRNA that has been cleaved from a microRNA precursor (a "pre-miRNA"), or that has been synthesized (e.g., synthesized in a laboratory by cell-free synthesis), and has a length of from about 19 nucleotides to about 27 nucleotides, e.g., a mature microRNA can have a length of 19 nt, 20 nt, 21 nt, 22 nt, 23 nt, 24 nt, 25 nt, 26 nt, or 27 nt. A mature microRNA can bind to a target mRNA and inhibit translation of the target mRNA.

"Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV.

The terms "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Generally, the genetic element is introduced into a chromosome or mini-chromosome in the cell; but any alteration that changes the phenotype and/or genotype of the cell and its progeny is included in this term.

A cell is said to be "stably" altered, transduced, genetically modified, or transformed with a genetic sequence if the sequence is available to perform its function during extended culture of the cell in vitro. Generally, such a cell is "heritably" altered (genetically modified) in that a genetic alteration is introduced which is also inheritable by progeny of the altered cell.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, which retains the desired biochemical function of the intact protein. Similarly, references to nucleic acids encoding anti-angiogenic polypeptides, nucleic acids encoding neuroprotective polypeptides, and other such nucleic acids for use in delivery of a gene product to a mammalian subject (which may be referred to as "transgenes" to be delivered to a recipient cell), include polynucleotides encoding the intact polypeptide or any fragment or genetically engineered derivative possessing the desired biochemical function.

An "isolated" plasmid, nucleic acid, vector, virus, virion, host cell, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this disclosure are increasingly more isolated. An isolated nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a mammalian cell" includes a plurality of such cells and reference to "the AAV virion" includes reference to one or more AAV virions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides an in vitro mammalian cell that is genetically modified to provide for enhanced production of adeno-associated virus (AAV) virions. The mammalian cells can be used to produce AAV virions, e.g., recombinant AAV virions that include a heterologous nucleic acid encoding a gene product; the present disclosure thus provides methods for producing an AAV virion, which may be a recombinant AAV virion. The present disclosure also provides methods for identifying genes that, when overexpressed or knocked out in a mammalian cell, provide for enhanced production of AAV by the mammalian cell.

Genetically Modified Mammalian Cells

The present disclosure provides an in vitro mammalian cell that is genetically modified to provide for enhanced production of AAV virions by the cell. In some cases, the genetic modification provides for increased synthesis of a gene product by the cell, compared to the amount of the gene product synthesized by a control cell that does not comprise the genetic modification. In some cases, the genetic modification provides for decreased synthesis of a gene product by the cell, compared to the amount of the gene product synthesized by a control cell that does not comprise the genetic modification.

In some cases, a genetically modified mammalian cell of the present disclosure comprises two or more genetic modifications that together result in enhanced production of AAV virions by the cell. For example, in some cases, a genetically modified mammalian cell of the present disclosure comprises: i) a first genetic modification that results in increased production of a first gene product compared to the level of production of the first gene product in a control mammalian cell that does not comprise the first genetic modification; and ii) a second genetic modification that results in increased production of a second gene product compared to the level of production of the second gene product in a control mammalian cell that does not comprise the second genetic modification. As another example, in some cases, a genetically modified mammalian cell of the present disclosure comprises: i) a first genetic modification that results in decreased production (e.g., results in a knock out) of a first gene product compared to the level of production of the first gene product in a control mammalian cell that does not comprise the first genetic modification; and ii) a second genetic modification that results in decreased production (e.g., results in a knock out) of a second gene product compared to the level of production of the second gene product in a control mammalian cell that does not comprise the second genetic modification. As another example, in some cases, a genetically modified mammalian cell of the present disclosure comprises: i) a first genetic modification that results in decreased production (e.g., results in a knock out) of a first gene product compared to the level of production of the first gene product in a control mammalian cell that does not comprise the first genetic modification; and ii) a second genetic modification that results in increased production of a second gene product compared to the level of production of the second gene product in a control mammalian cell that does not comprise the second genetic modification.

A genetically modified mammalian cell of the present disclosure provides for enhanced production of AAV virions by the cell. For example, when a genetically modified mammalian cell of the present disclosure comprises an AAV genome (or a recombinant AAV genome, as described below), and is provided with helper functions, the genetically modified mammalian cell produces AAV virions (which may be recombinant AAV virions) at a level that is at least 25%, at least 50%, at least 75%, at least 2-fold, at least 2.5-fold, at least 3-fold, at least 4-fold, at least 5-fold, from about 5-fold to about 10-fold, or more than 10-fold, higher than the amount of AAV virions produced by a control cell not comprising the genetic modification(s).

Overexpressed Gene Products

Genetic modifications that result in increased production of a gene product include, e.g., insertion into the genome of a mammalian cell of an exogenous nucleic acid comprising a nucleotide sequence encoding the gene product.

Non-limiting examples of gene products that, when overexpressed in a mammalian cell, provide for increased production of AAV virions by the cell, compared to the level of production of AAV virions by a control cell not genetically modified to overexpress the gene product, include, but are not limited to, a spindle and kinetochore associated complex subunit 2 (SKA2) polypeptide; an Inositol Tri-Phosphate Receptor Interacting Protein (ITPRIP2; also referred to herein as "ITPRIP") polypeptide; a CUGBP, Elav-like family member 2 (CELF2) polypeptide; a centrosomal protein 128 (CEP128) polypeptide; a protocadherin alpha 2 (PCDHA2) polypeptide; and an acetylcholinesterase (Cartwright blood group) (ACHE) polypeptide For example, in some cases, a mammalian cell of the present disclosure comprises a genetic modification that provides for increased production of a SKA2 polypeptide, compared to the level of the SKA2 polypeptide produced by a control cell not comprising the genetic modification. In some cases, a nucleic acid comprising a nucleotide sequence encoding a SKA2 polypeptide is introduced into a recipient mammalian cell, generating a genetically modified mammalian cell that produces the SKA2 polypeptide at a level that is at least 20%, at least 25%, at least 50%, at least 75%, at least 2-fold, at least 5-fold, at least 10-fold, at least 25-fold, or more than 25-fold, higher than the level of SKA2 polypeptide produced by the recipient (unmodified) cell. All or a portion of the nucleic acid comprising the nucleotide sequence encoding the SKA2 polypeptide can integrate into the genome of the genetically modified cell. Alternatively, the nucleic acid comprising the nucleotide sequence encoding the SKA2 polypeptide can be present in the genetically modified cell episomally (not integrated into the genome of the genetically modified cell. The nucleotide sequence encoding the SKA2 polypeptide can be operably linked to a constitutive promoter or a regulatable (e.g., inducible) promoter. Amino acid sequences of SKA2 polypeptides are known in the art. See, e.g., GenBank Accession No. NP_001094065. In some cases, the SKA2 polypeptide comprises an amino acid sequence having at least 85%, at least 90%, at least 95%, at least 98%, at least 99%, or 100%, amino acid sequence identity to the following SKA2 amino acid sequence:

(SEQ ID NO: 1)
MASEVGHNLE SPETPGGGGW TRVEFPPPAP KGAATVWCLN

RLGSRKLSLI WITFNTGWNM KSRLIILIQQ VSCHH.

As another example, in some cases, a mammalian cell of the present disclosure comprises a genetic modification that provides for increased production of an ITPRIP2 polypeptide, compared to the level of the ITPRIP2 polypeptide produced by a control cell not comprising the genetic modification. In some cases, a nucleic acid comprising a nucleotide sequence encoding a ITPRIP2 polypeptide is introduced into a recipient mammalian cell, generating a genetically modified mammalian cell that produces the ITPRIP2 polypeptide at a level that is at least 20%, at least 25%, at least 50%, at least 75%, at least 2-fold, at least 5-fold, at least 10-fold, at least 25-fold, or more than 25-fold, higher than the level of ITPRIP2 polypeptide produced by the recipient (unmodified) cell. All or a portion of the nucleic acid comprising the nucleotide sequence encoding the ITPRIP2 polypeptide can integrate into the genome of the genetically modified cell. Alternatively, the nucleic acid comprising the nucleotide sequence encoding the ITPRIP2 polypeptide can be present in the genetically modified cell episomally (not integrated into the genome of the genetically modified cell. The nucleotide sequence encoding the ITPRIP2 polypeptide can be operably linked to a constitutive promoter or a regulatable (e.g., inducible) promoter. Amino acid sequences of ITPRIP2 polypeptides are known in the art. In some cases, the ITPRIP2 polypeptide comprises an amino acid sequence having at least 85%, at least 90%, at least 95%, at least 98%, at least 99%, or 100%, amino acid sequence identity to the ITPRIP2 amino acid sequence depicted in FIG. 6.

In some cases, a genetically modified mammalian cell of the present disclosure comprises a genetic modification that results in increased production of a SKA2 polypeptide, compared to the level of the SKA2 polypeptide produced by a control cell not comprising the genetic modification, where the genetically modified mammalian cell does not comprise any other genetic modifications that provide for increased production of an AAV virion by the cell. In some cases, a genetically modified mammalian cell of the present disclosure comprises a genetic modification that results in increased production of a ITPRIP2 polypeptide, compared to the level of the ITPRIP2 polypeptide produced by a control cell not comprising the genetic modification, where the genetically modified mammalian cell does not comprise any other genetic modifications that provide for increased production of an AAV virion by the cell. In some cases, a mammalian cell of the present disclosure comprises: i) a first genetic modification that results in increased production of a SKA2 polypeptide, compared to the level of the SKA2 polypeptide produced by a control cell not comprising the first genetic modification; and ii) a second genetic modification that results in increased production of a ITPRIP2 polypeptide, compared to the level of the ITPRIP2 polypeptide produced by a control cell not comprising the second genetic modification.

As another example, in some cases, a mammalian cell of the present disclosure comprises a genetic modification that provides for increased production of a CELF2 polypeptide, compared to the level of the CELF2 polypeptide produced by a control cell not comprising the genetic modification. In some cases, a nucleic acid comprising a nucleotide sequence encoding a CELF2 polypeptide is introduced into a recipient mammalian cell, generating a genetically modified mammalian cell that produces the CELF2 polypeptide at a level that is at least 20%, at least 25%, at least 50%, at least 75%, at least 2-fold, at least 5-fold, at least 10-fold, at least 25-fold, or more than 25-fold, higher than the level of CELF2 polypeptide produced by the recipient (unmodified) cell. All or a portion of the nucleic acid comprising the nucleotide sequence encoding the CELF2 polypeptide can integrate into the genome of the genetically modified cell. Alternatively, the nucleic acid comprising the nucleotide sequence encoding the CELF2 polypeptide can be present in the genetically modified cell episomally (not integrated into the genome of the genetically modified cell. The nucleotide sequence encoding the CELF2 polypeptide can be operably linked to a constitutive promoter or a regulatable (e.g., inducible) promoter. Amino acid sequences of CELF2 polypeptides are known in the art. In some cases, the CELF2 polypeptide comprises an amino acid sequence having at least 85%, at least 90%, at least 95%, at least 98%, at least 99%, or 100%, amino acid sequence identity to the CELF2 amino acid sequence depicted in FIG. 7.

As another example, in some cases, a mammalian cell of the present disclosure comprises a genetic modification that provides for increased production of a CEP128 polypeptide, compared to the level of the CEP128 polypeptide produced by a control cell not comprising the genetic modification. In some cases, a nucleic acid comprising a nucleotide sequence encoding a CEP128 polypeptide is introduced into a recipient mammalian cell, generating a genetically modified mammalian cell that produces the CEP128 polypeptide at a level that is at least 20%, at least 25%, at least 50%, at least 75%, at least 2-fold, at least 5-fold, at least 10-fold, at least 25-fold, or more than 25-fold, higher than the level of CEP128 polypeptide produced by the recipient (unmodified) cell. All or a portion of the nucleic acid comprising the nucleotide sequence encoding the CEP128 polypeptide can integrate into the genome of the genetically modified cell. Alternatively, the nucleic acid comprising the nucleotide sequence encoding the CEP128 polypeptide can be present in the genetically modified cell episomally (not integrated into the genome of the genetically modified cell. The nucleotide sequence encoding the CEP128 polypeptide can be operably linked to a constitutive promoter or a regulatable (e.g., inducible) promoter. Amino acid sequences of CEP128 polypeptides are known in the art. In some cases, the CEP128 polypeptide comprises an amino acid sequence having at least 85%, at least 90%, at least 95%, at least 98%, at least 99%, or 100%, amino acid sequence identity to the CEP128 amino acid sequence depicted in FIG. 8.

As another example, in some cases, a mammalian cell of the present disclosure comprises a genetic modification that provides for increased production of a PCDHA2 polypeptide, compared to the level of the PCDHA2 polypeptide produced by a control cell not comprising the genetic modification. In some cases, a nucleic acid comprising a nucleotide sequence encoding a PCDHA2 polypeptide is introduced into a recipient mammalian cell, generating a genetically modified mammalian cell that produces the PCDHA2 polypeptide at a level that is at least 20%, at least 25%, at least 50%, at least 75%, at least 2-fold, at least 5-fold, at least 10-fold, at least 25-fold, or more than 25-fold, higher than the level of PCDHA2 polypeptide produced by the recipient (unmodified) cell. All or a portion of the nucleic acid comprising the nucleotide sequence encoding the PCDHA2 polypeptide can integrate into the genome of the genetically modified cell. Alternatively, the nucleic acid comprising the nucleotide sequence encoding the PCDHA2 polypeptide can be present in the genetically modified cell episomally (not integrated into the genome of the genetically modified cell. The nucleotide sequence encoding the PCDHA2 polypeptide can be operably linked to a constitutive promoter or a regulatable (e.g., inducible) promoter. Amino acid sequences of PCDHA2 polypeptides are known in the art. In some cases, the PCDHA2 polypeptide comprises an amino acid sequence having at least 85%, at least 90%, at least 95%, at least 98%, at least 99%, or 100%, amino acid sequence identity to the PCDHA2 amino acid sequence depicted in FIG. 9.

As another example, in some cases, a mammalian cell of the present disclosure comprises a genetic modification that provides for increased production of a ACHE polypeptide, compared to the level of the ACHE polypeptide produced by a control cell not comprising the genetic modification. In some cases, a nucleic acid comprising a nucleotide sequence encoding a ACHE polypeptide is introduced into a recipient mammalian cell, generating a genetically modified mammalian cell that produces the ACHE polypeptide at a level that is at least 20%, at least 25%, at least 50%, at least 75%, at least 2-fold, at least 5-fold, at least 10-fold, at least 25-fold, or more than 25-fold, higher than the level of ACHE polypeptide produced by the recipient (unmodified) cell. All or a portion of the nucleic acid comprising the nucleotide sequence encoding the ACHE polypeptide can integrate into the genome of the genetically modified cell. Alternatively, the nucleic acid comprising the nucleotide sequence encoding the ACHE polypeptide can be present in the genetically modified cell episomally (not integrated into the genome of the genetically modified cell. The nucleotide sequence encoding the ACHE polypeptide can be operably linked to a constitutive promoter or a regulatable (e.g., inducible) promoter. Amino acid sequences of ACHE polypeptides are known in the art. In some cases, the ACHE polypeptide comprises an amino acid sequence having at least 85%, at least 90%, at least 95%, at least 98%, at least 99%, or 100%, amino acid sequence identity to the ACHE amino acid sequence depicted in FIG. 10.

As noted above, in some cases, a nucleotide sequence encoding a polypeptide that, when overexpressed, provides for increased production of an AAV virion in a genetically modified mammalian cell of the present disclosure, is operably linked to a transcriptional control element such as a promoter. Suitable promoters include constitutively active promoters (i.e., a promoter that is constitutively in an active/"ON" state). Suitable promoters include inducible promoters (i.e., a promoter whose state, active/"ON" or inactive/"OFF", is controlled by an external stimulus, e.g., the presence of a particular temperature, compound, or protein). Suitable promoter and enhancer elements are known in the art.

Suitable reversible promoters, including reversible inducible promoters are known in the art. Such reversible promoters may be isolated and derived from many organisms, e.g., eukaryotes and prokaryotes. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), temperature regulated promoters (e.g., heat shock inducible promoters (e.g., HSP-70, HSP-90, soybean heat shock promoter, etc.), light regulated promoters, synthetic inducible promoters, and the like.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), and temperature/heat-inducible promoters (e.g., heat shock promoters).

Knock-Out of a Gene Product

Genetic modifications that result in reduced production (e.g., knock-out) of a gene product include, e.g., deletion of all or a portion of a coding region encoding the gene product; insertion of one or more nucleotides such that the coding region encoding the gene product is out of frame; and the like.

Genes that, when disrupted, result in: i) reduced production of a gene product encoded by the gene; and ii) increased production of an AAV virion by a mammalian cell comprising a genetic modification that disrupts the gene, include, but are not limited to, an endoplasmic reticulum lectin 1 (ER-LEC1) gene (e.g., Gene ID 27248), a kinesin-like protein (KIF23) gene (e.g., Gene ID 9493), an interferon-induced protein with tetratricopeptide repeats 5 (IFIT5) gene (e.g., Gene ID 24138), a caspase recruitment domain-containing protein 8 (CARD8) gene (e.g., Gene ID 22900), a gene encoding hsa-mir-4770 (e.g., Gene ID 100616373), and a chromosome 5 open reading frame (C5orf52) gene (e.g., Gene ID 100190949).

In some cases, a genetically modified mammalian cell of the present disclosure comprises a genetic modification that provides for reduced production of an ERLEC1 polypeptide, compared to the level of the ERLEC1 polypeptide produced by a control cell not comprising the genetic modification. In some cases, a genetic modification is made in a recipient mammalian cell, generating a genetically modified mammalian cell that produces the ERLEC1 polypeptide at a level that is at least 50% less, at least 75% less, at least 80% less, at least 90% less, at least 95% less, at least 98% less, or at least 99% less, than the level of ERLEC1 polypeptide produced by the recipient (unmodified) cell. In some cases, an ERLEC1 polypeptide is not produced in a genetically modified mammalian cell of the present disclosure or is produced at undetectable levels. In some cases, a CRISPR/Cas effector polypeptide and one or more guide RNAs are introduced into a recipient mammalian cell, where the CRISPR/Cas effector polypeptide and guide RNA(s) provide for deletion or all or a part of a coding region for the ERLEC1 polypeptide. Amino acid sequences of ERLEC1 polypeptides are known in the art. In some cases, the ERLEC1 polypeptide comprises an amino acid sequence having at least 85%, at least 90%, at least 95%, at least 98%, at least 99%, or 100%, amino acid sequence identity to the ERLEC1 amino acid sequence depicted in FIG. 11. Guide RNAs that target an ERLEC1 gene can be readily generated by those skilled in the art, given the known genomic structure and genomic sequence of an ERLEC1 gene.

In some cases, a genetically modified mammalian cell of the present disclosure comprises a genetic modification that provides for reduced production of a KIF23 polypeptide, compared to the level of the KIF23 polypeptide produced by a control cell not comprising the genetic modification. In some cases, a genetic modification is made in a recipient mammalian cell, generating a genetically modified mammalian cell that produces the KIF23 polypeptide at a level that is at least 50% less, at least 75% less, at least 80% less, at least 90% less, at least 95% less, at least 98% less, or at least 99% less, than the level of KIF23 polypeptide produced by the recipient (unmodified) cell. In some cases, a KIF23 polypeptide is not produced in a genetically modified mammalian cell of the present disclosure or is produced at undetectable levels. In some cases, a CRISPR/Cas effector polypeptide and one or more guide RNAs are introduced into a recipient mammalian cell, where the CRISPR/Cas effector polypeptide and guide RNA(s) provide for deletion or all or a part of a coding region for the KIF23 polypeptide. Amino acid sequences of KIF23 polypeptides are known in the art. In some cases, the KIF23 polypeptide comprises an amino acid sequence having at least 85%, at least 90%, at least 95%, at least 98%, at least 99%, or 100%, amino acid sequence identity to the KIF23 amino acid sequence depicted in FIG. 12. Guide RNAs that target a KIF23 gene can be readily generated by those skilled in the art, given the known genomic structure and genomic sequence of a KIF23 gene.

In some cases, a genetically modified mammalian cell of the present disclosure comprises a genetic modification that provides for reduced production of an IFIT5 polypeptide, compared to the level of the IFIT5 polypeptide produced by a control cell not comprising the genetic modification. In some cases, a genetic modification is made in a recipient mammalian cell, generating a genetically modified mammalian cell that produces the IFIT5 polypeptide at a level that is at least 50% less, at least 75% less, at least 80% less, at least 90% less, at least 95% less, at least 98% less, or at least 99% less, than the level of IFIT5 polypeptide produced by the recipient (unmodified) cell. In some cases, an IFIT5 polypeptide is not produced in a genetically modified mammalian cell of the present disclosure or is produced at undetectable levels. In some cases, a CRISPR/Cas effector polypeptide and one or more guide RNAs are introduced into a recipient mammalian cell, where the CRISPR/Cas effector polypeptide and guide RNA(s) provide for deletion or all or a part of a coding region for the IFIT5 polypeptide. Amino acid sequences of IFIT5 polypeptides are known in the art. In some cases, the IFIT5 polypeptide comprises an amino acid sequence having at least 85%, at least 90%, at least 95%, at least 98%, at least 99%, or 100%, amino acid sequence identity to the IFIT5 amino acid sequence depicted in FIG. 13. Guide RNAs that target an IFIT5 gene can be readily generated by those skilled in the art, given the known genomic structure and genomic sequence of an IFIT5 gene.

In some cases, a genetically modified mammalian cell of the present disclosure comprises a genetic modification that provides for reduced production of a CARD8 polypeptide, compared to the level of the CARD8 polypeptide produced by a control cell not comprising the genetic modification. In some cases, a genetic modification is made in a recipient mammalian cell, generating a genetically modified mammalian cell that produces the CARD8 polypeptide at a level that is at least 50% less, at least 75% less, at least 80% less, at least 90% less, at least 95% less, at least 98% less, or at least 99% less, than the level of CARD8 polypeptide produced by the recipient (unmodified) cell. In some cases, a CARD8 polypeptide is not produced in a genetically modified mammalian cell of the present disclosure or is produced at undetectable levels. In some cases, a CRISPR/Cas effector polypeptide and one or more guide RNAs are introduced into a recipient mammalian cell, where the CRISPR/Cas effector polypeptide and guide RNA(s) provide for deletion or all or a part of a coding region for the CARD8 polypeptide. Amino acid sequences of CARD8 polypeptides are known in the art. In some cases, the CARD8 polypeptide comprises an amino acid sequence having at least 85%, at least 90%, at least 95%, at least 98%, at least 99%, or 100%, amino acid sequence identity to the CARD8 amino acid sequence depicted in FIG. 14. Guide RNAs that target a CARD8 gene can be readily generated by those skilled in the art, given the known genomic structure and genomic sequence of a CARD8 gene.

In some cases, a genetically modified mammalian cell of the present disclosure comprises a genetic modification that provides for reduced production of a C5orf52 polypeptide, compared to the level of the C5orf52 polypeptide produced by a control cell not comprising the genetic modification. In some cases, a genetic modification is made in a recipient mammalian cell, generating a genetically modified mammalian cell that produces the C5orf52 polypeptide at a level that is at least 50% less, at least 75% less, at least 80% less, at least 90% less, at least 95% less, at least 98% less, or at least 99% less, than the level of C5orf52 polypeptide produced by the recipient (unmodified) cell. In some cases, a C5orf52 polypeptide is not produced in a genetically modified mammalian cell of the present disclosure or is produced at undetectable levels. In some cases, a CRISPR/Cas effector polypeptide and one or more guide RNAs are introduced into a recipient mammalian cell, where the CRISPR/Cas effector polypeptide and guide RNA(s) provide for deletion or all or a part of a coding region for the C5orf52 polypeptide. Amino acid sequences of C5orf52 polypeptides are known in the art. In some cases, the C5orf52 polypeptide comprises an amino acid sequence having at least 85%, at least 90%, at least 95%, at least 98%, at least 99%, or 100%, amino acid sequence identity to the C5orf52 amino acid sequence depicted in FIG. 15. Guide RNAs that target a C5orf52 gene can be readily generated by those skilled in the art, given the known genomic structure and genomic sequence of a C5orf52 gene.

In some cases, a genetically modified mammalian cell of the present disclosure comprises a genetic modification that provides for reduced production of hsa-mir4770 microRNA. compared to the level of the hsa-mir4770 microRNA produced by a control cell not comprising the genetic modification. In some cases, a genetic modification is made in a recipient mammalian cell, generating a genetically modified mammalian cell that produces the hsa-mir4770 at a level that is at least 50% less, at least 75% less, at least 80% less, at least 90% less, at least 95% less, at least 98% less, or at least 99% less, than the level of hsa-mir4770 produced by the recipient (unmodified) cell. In some cases, a hsa-mir4770 is not produced in a genetically modified mammalian cell of the present disclosure or is produced at undetectable levels. In some cases, a CRISPR/Cas effector polypeptide and one or more guide RNAs are introduced into a recipient mammalian cell, where the CRISPR/Cas effector polypeptide and guide RNA(s) provide for deletion or all or a part of a coding region for hsa-mir4770. In some cases, the hsa-mir4770 comprises a nucleotide acid sequence having at least 85%, at least 90%, at least 95%, at least 98%, at least 99%, or 100%, nucleotide sequence identity to the following hsa-mir4770 nucleotide sequence: GAGUUAUGGGGUCAUC-UAUCCUUCCCUUGGAAAAUGAUCUGAGAUGACA-CUGUAGCUC (SEQ ID NO: 2). Guide RNAs that target a hsa-mir4770-encoding gene can be readily generated by those skilled in the art, given the sequence of hsa-mir4770.

Recipient Cells

Cells ("recipient cells") that can be used to generate a genetically modified mammalian cell of the present disclosure include any mammalian cell that can be cultured in vitro and that can produce an AAV virion. A recipient cell is genetically modified, as described above, to provide for increased production of an AAV virion, compared to the level of production of the AAV virion by a control cell not comprising the genetic modification. Examples of suitable recipient cells include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

AAV Virions

A genetically modified mammalian cell of the present disclosure can comprise an AAV genome. In some cases, the AAV genome is a wild-type AAV genome; e.g., where the AAV genome comprises a nucleotide sequence of a naturally-occurring AAV. A genetically modified mammalian cell of the present disclosure can comprise a recombinant AAV genome, e.g., an AAV genome in which part of the AAV genome is replaced with a heterologous nucleic acid.

Recombinant AAV and Recombinant AAV Virions

In some cases, a genetically modified mammalian cell of the present disclosure comprises: a) a nucleic acid comprising a nucleotide sequence encoding an AAV capsid; and b) a heterologous nucleic acid (e.g., a nucleic acid comprising a nucleotide sequence encoding a gene product that is heterologous to AAV, i.e., a gene product that is not encoded by a naturally occurring AAV). In some cases, the heterologous gene product is a nucleic acid. In some cases, the heterologous gene product is a polypeptide.

In some cases, a genetically modified mammalian cell of the present disclosure comprises: a) a nucleic acid comprising a nucleotide sequence encoding an AAV capsid, where the AAV capsid is a variant AAV capsid that provides for one or more of: i) increased infectivity of a non-permissive cell compared to the infectivity of the non-permissive cell by an AAV virion comprising a wild-type AAV capsid protein; ii) reduced susceptibility to neutralization by a neutralizing antibody specific; and iii) increased ability to cross a physiological barrier (e.g., blood-brain barrier; inner limiting membrane; and the like); and b) a heterologous nucleic acid comprising a nucleotide sequence encoding a heterologous gene product. Such a genetically modified mammalian cell can produce a recombinant AAV virion (rAAV virion).

A recombinant AAV (rAAV) (or an rAAV virion produced by a genetically modified mammalian cell of the present disclosure) comprises a heterologous nucleic acid comprising a nucleotide sequence encoding one or more gene products (one or more heterologous gene products). In some cases, the gene product is a polypeptide. In some cases, the gene product is an RNA. In some cases, an rAAV (or an rAAV virion produced by a genetically modified mammalian cell of the present disclosure) comprises a heterologous nucleotide sequence encoding both a heterologous nucleic acid gene product and a heterologous polypeptide gene product. Where the gene product is an RNA, in some cases, the RNA gene product encodes a polypeptide. Where the gene product is an RNA, in some cases, the RNA gene product does not encode a polypeptide. In some cases, an rAAV (or an rAAV virion produced by a genetically modified mammalian cell of the present disclosure) comprises a single heterologous nucleic acid comprising a nucleotide sequence encoding a single heterologous gene product. In some cases, an rAAV (or an rAAV virion produced by a genetically modified mammalian cell of the present disclosure) comprises a single heterologous nucleic acid comprising a nucleotide sequence encoding two heterologous gene products. Where the single heterologous nucleic acid encodes two heterologous gene products, in some cases, nucleotide sequences encoding the two heterologous gene products are operably linked to the same promoter. Where the single heterologous nucleic acid encodes two heterologous gene products, in some cases, nucleotide sequences encoding the two heterologous gene products are operably linked to two different promoters. In some cases, an rAAV (or an rAAV virion produced by a genetically modified mammalian cell of the present disclosure) comprises a single heterologous nucleic acid comprising a nucleotide sequence encoding three heterologous gene products. Where the single heterologous nucleic acid encodes three heterologous gene products, in some cases, nucleotide sequences encoding the three heterologous gene products are operably linked to the same promoter. Where the single heterologous nucleic acid encodes three heterologous gene products, in some cases, nucleotide sequences encoding the three heterologous gene products are operably linked to two or three different promoters. In some cases, an rAAV (or an rAAV virion produced by a genetically modified mammalian cell of the present disclosure) comprises two heterologous nucleic acids, each comprising a nucleotide sequence encoding a heterologous gene product.

In some cases, the gene product is a polypeptide-encoding RNA. In some cases, the gene product is an interfering RNA. In some cases, the gene product is an aptamer. In some cases, the gene product is a polypeptide. In some cases, the gene product is a therapeutic polypeptide, e.g., a polypeptide that provides clinical benefit. In some cases, the gene product is a site-specific nuclease that provide for site-specific knock-down of gene function. In some embodiments, the gene product is a CRISPR/Cas effector polypeptide that provides for modification of a target nucleic acid. In some cases, the gene products are: i) a CRISPR/Cas effector polypeptide that provides for modification of a target nucleic acid; and ii) a guide RNA that comprises a first segment that binds to a target sequence in a target nucleic acid and a second segment that binds to the CRISPR/Cas effector polypeptide. In some cases, the gene products are: i) a CRISPR/Cas effector polypeptide that provides for modification of a target nucleic acid; ii) a first guide RNA that comprises a first segment that binds to a first target sequence in a target nucleic acid and a second segment that binds to the CRISPR/Cas effector polypeptide; and iii) a first guide RNA that comprises a first segment that binds to a second target sequence in the target nucleic acid and a second segment that binds to the CRISPR/Cas effector polypeptide. CRISPR/Cas effector polypeptides include type II CRISPR/Cas effector polypeptides (e.g., Cas9 polypeptides); type V CRISPR/Cas effector polypeptides (e.g., a Cas12a polypeptide; a Cas12b polypeptide; a Cas12c polypeptide; a Cas12d polypeptide; a Cas12e polypeptide; a Cas13a polypeptide); a CasX polypeptide; a CasY polypeptide; and a CasZ polypeptide.

A nucleotide sequence encoding a heterologous gene product in an rAAV virion of the present disclosure can be operably linked to a promoter. For example, a nucleotide sequence encoding a heterologous gene product in an rAAV virion can be operably linked to a constitutive promoter, a regulatable promoter, a tissue-specific promoter, or a cell type-specific promoter.

Suitable nucleic acid gene products include interfering RNA, antisense RNA, ribozymes, CRISPR/Cas guide RNAs, and aptamers. Where the gene product is an interfering RNA (RNAi), suitable RNAi include RNAi that decrease the level of an angiogenic factor in a cell. For example, an RNAi can be a miRNA, an shRNA, or an siRNA that reduces the level of vascular endothelial growth factor (VEGF) in a cell.

Where the gene product is a polypeptide, exemplary polypeptides include, e.g., an interferon (e.g., IFN-γ, IFN-α, IFN-β, IFN-ω; IFN-τ); an insulin (e.g., Novolin, Humulin, Humalog, Lantus, Ultralente, etc.); an erythropoietin ("EPO"; e.g., Procrit®, Eprex®, or Epogen® (epoetin-α); Aranesp® (darbepoietin-α); NeoRecormon®, Epogin® (epoetin-β); and the like); an antibody (e.g., a monoclonal antibody) (e.g., Rituxan® (rituximab); Remicade® (infliximab); Herceptin® (trastuzumab); Humira™ (adalimumab); Xolair® (omalizumab); Bexxar® (tositumomab); Raptiva™ (efalizumab); Erbitux™ (cetuximab); and the like), including an antigen-binding fragment of a monoclonal antibody; a blood factor (e.g., Activase® (alteplase) tissue plasminogen activator; NovoSeven® (recombinant human factor VIIa); Factor VIIa; Factor VIII (e.g., Kogenate®); Factor IX; β-globin; hemoglobin; and the like); a colony stimulating factor (e.g., Neupogen® (filgrastim; G-CSF); Neulasta (pegfilgrastim); granulocyte colony stimulating factor (G-CSF), granulocyte-monocyte colony stimulating factor, macrophage colony stimulating factor, megakaryocyte colony stimulating factor; and the like); a growth hormone (e.g., a somatotropin, e.g., Genotropin®, Nutropin®, Norditropin®, Saizen®, Serostim®, Humatrope®, etc.; a human growth hormone; and the like); an interleukin (e.g., IL-1; IL-2, including, e.g., Proleukin@; IL-3, IL-4, IL-5, IL-6, IL-7, IL-8, IL-9; etc.); a growth factor (e.g., Regranex® (beclapermin; PDGF); Fiblast® (trafermin; bFGF); Stemgen® (ancestim; stem cell factor); keratinocyte growth factor; an acidic fibroblast growth factor, a stem cell factor, a basic fibroblast growth factor, a hepatocyte growth factor; and the like); a soluble receptor (e.g., a TNF-α-binding soluble receptor such as Enbrel@(etanercept); a soluble VEGF receptor; a soluble interleukin receptor; a soluble γ/δ T cell receptor; and the like); an enzyme (e.g., α-glucosidase; Cerazyme® (imiglucarase; β-glucocerebrosidase, Ceredase® (alglucerase; ); an enzyme activator (e.g., tissue plasminogen activator); a chemokine (e.g., IP-10; Mig; Groα/IL-8, RANTES; MIP-1α; MIP-1β; MCP-1; PF-4; and the like); an angiogenic agent (e.g., vascular endothelial growth factor (VEGF); an anti-angiogenic agent (e.g., a soluble VEGF receptor); a protein vaccine; a neuroactive peptide such as bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, neurotensin, motilin, thyrotropin, neuropeptide Y, luteinizing hormone, calcitonin, insulin, glucagon, vasopressin, angiotensin II, thyrotropin-releasing hormone, vasoactive intestinal peptide, a sleep peptide, etc.; other proteins such as a thrombolytic agent, an atrial natriuretic peptide, bone morphogenic protein, thrombopoietin, relaxin, glial fibrillary acidic protein, follicle stimulating hormone, a human alpha-1 antitrypsin, a leukemia inhibitory factor, a transforming growth factor, an insulin-like growth factor, a luteinizing hormone, a macrophage activating factor, tumor necrosis factor, a neutrophil chemotactic factor, a nerve growth factor a tissue inhibitor of metalloproteinases; a vasoactive intestinal peptide, angiogenin, angiotropin, fibrin; hirudin; a leukemia inhibitory factor; an IL-1 receptor antagonist (e.g., Kineret® (anakinra)); an ion channel, e.g., cystic fibrosis transmembrane conductance regulator (CFTR); dystrophin; utrophin, a tumor suppressor; lysosomal enzyme acid α-glucosidase (GAA); and the like. Suitable nucleic acids also include those that encode a functional fragment of any of the aforementioned proteins; and nucleic acids that encode functional variants of any of the aforementioned proteins.

Where the gene product is a polypeptide, exemplary polypeptides include neuroprotective polypeptides and anti-angiogenic polypeptides. Suitable polypeptides include, but are not limited to, glial derived neurotrophic factor (GDNF), fibroblast growth factor 2 (FGF-2), nurturin, ciliary neurotrophic factor (CNTF), nerve growth factor (NGF; e.g., nerve growth factor-β), brain derived neurotrophic factor (BDNF), neurotrophin-3 (NT-3), neurotrophin-4 (NT-4), neurotrophin-6 (NT-6), epidermal growth factor (EGF), pigment epithelium derived factor (PEDF), a Wnt polypeptide, soluble Flt-1, angiostatin, endostatin, an anti-VEGF antibody, a soluble VEGFR, and a member of the hedgehog family (sonic hedgehog, indian hedgehog, and desert hedgehog, etc.).

Where the rAAV virion comprises a variant capsid protein, in some cases, the variant AAV capsid protein comprises from 1 to about 10 amino acid differences (e.g., amino acid substitutions and/or amino acid insertions and/or amino acid deletions) compared to a wild-type AAV capsid protein. The amino acid difference(s) can be located in a solvent accessible site in the capsid, e.g., a solvent-accessible loop. For example, the amino acid substitution(s) can be located in a GH loop in the AAV capsid protein. As one non-limiting example, the variant capsid protein can comprise an amino acid substitution at amino acid 451 of AAV6 capsid, or the corresponding position in another AAV serotype. As another non-limiting example, the variant capsid protein can comprise an amino acid substitution at amino acid 532 of AAV6 capsid, or the corresponding position in another AAV serotype. In some cases, the variant capsid comprises an insertion of a peptide comprising LGETTRP, where the insertion site is between amino acids corresponding to 570 and 611 of VP1 of AAV2, or the corresponding position in the capsid protein of another AAV serotype. In some cases, the variant capsid comprises an insertion of a peptide comprising LAL-GETTRPA, where the insertion site is between amino acids corresponding to 570 and 611 of VP1 of AAV2, or the corresponding position in the capsid protein of another AAV serotype. See, e.g., U.S. Pat. Nos. 9,193,956; 8,663,624; and 9,457,103.

Method of Producing an AAV Virion

The present disclosure provides a method for producing an AAV virion, the method comprising: a) culturing a genetically modified mammalian cell of the present disclosure in vitro in a liquid culture medium, where the genetically modified mammalian cell comprises an AAV genome, such that the genetically modified mammalian cell produces an AAV virion comprising the AAV genome; and b) harvesting the AAV virion from the culture medium. In some cases, the genetically modified mammalian cell comprises: a) a nucleic acid comprising a nucleotide sequence encoding an AAV capsid; and b) a heterologous nucleic acid comprising a nucleotide sequence encoding one or more heterologous gene products. In some cases, the AAV capsid is a variant AAV capsid. In some cases, the one or more heterologous gene products is a nucleic acid. In some cases, the one or more heterologous gene products is a polypeptide. In some cases, the heterologous gene products comprise a nucleic acid gene product and a polypeptide gene product.

A genetically modified mammalian cell of the present disclosure can function as "producer" cell for AAV vector replication and packaging. Such a producer cell generally comprises or is modified to comprise several different types of components for AAV (including rAAV) production. As noted above, in some cases, a genetically modified mammalian cell of the present disclosure can comprise an AAV genome or a recombinant adeno-associated viral (rAAV) vector genome (or "rAAV pro-vector") that can be replicated and packaged into particles by the host packaging cell. The rAAV pro-vector comprises a heterologous nucleic acid (or "transgene"), where the heterologous nucleic acid can be flanked by two AAV inverted terminal repeats (ITRs) which comprise sequences that are recognized during excision, replication and packaging of the AAV vector, as well as during integration of the vector into a host cell genome.

A second component is a helper virus that can provide helper functions for AAV replication, or a helper recombinant vector that comprises a nucleotide sequence encoding helper functions. Although adenovirus is commonly employed, other helper viruses can also be used as is known in the art. Alternatively, the requisite helper virus functions can be isolated genetically from a helper virus and the encoding genes can be used to provide helper virus functions in trans. The AAV vector elements and the helper virus (or helper virus functions) can be introduced into the host cell either simultaneously or sequentially in any order.

The final components for AAV production to be provided in the producer cell are "AAV packaging genes" such as AAV rep and cap genes that provide replication and encapsidation proteins, respectively. Several different versions of AAV packaging genes can be provided (including rep-cap cassettes and separate rep and/or cap cassettes in which the rep and/or cap genes can be left under the control of the native promoters or operably linked to heterologous promoters. Such AAV packaging genes can be introduced either transiently or stably into the host packaging cell (e.g., a genetically modified mammalian cell of the present disclosure), as is known in the art.

In some cases, a genetically modified mammalian cell of the present disclosure is further genetically modified with one or more nucleic acids comprising nucleotide sequences encoding one or more of: AAV rep proteins; and AAV cap protein. In some cases, such nucleic acids encoding helper functions are integrated into the genome of a genetically modified mammalian cell of the present disclosure.

To produce an AAV virion (which may be an rAAV virion), a genetically modified mammalian cell of the present disclosure (where the genetically modified mammalian cell comprises an AAV genome; or comprises: a) a nucleic acid comprising a nucleotide sequence encoding an AAV capsid; and b) a heterologous nucleic acid comprising a nucleotide sequence encoding one or more heterologous gene products) is modified with a helper virus or one or more recombinant expression vectors comprising nucleotide sequences encoding helper functions. Thus, in some cases, a method of the present disclosure comprises: A) culturing a genetically modified mammalian cell of the present disclosure in vitro in a liquid culture medium, where the genetically modified mammalian cell comprises: a) an AAV genome; or b) i) a nucleic acid comprising a nucleotide sequence encoding an AAV capsid; and ii) a heterologous nucleic acid comprising a nucleotide sequence encoding one or more heterologous gene products; B) introducing into the genetically modified mammalian cell a nucleic acid comprising a nucleotide sequence encoding helper functions, such that the genetically modified mammalian cell produces an AAV virion or an rAAV virion; and C) harvesting the AAV virion from the culture medium.

In some cases, the harvested AAV virions are purified. In some cases, the AAV virions are purified to at least 80%, at least 90%, at least 95%, at least 98%, at least 99%, or greater than 99%, purity.

Suitable liquid culture media include any culture medium that provides for growth and/or viability of a mammalian cell in in vitro culture.

Methods of Identifying Genes that, when Overexpressed, Provide for Increased Production of AAV Virions The present disclosure provides a method of identifying a gene product that, when overexpressed, enhances production of a virus by a mammalian cell. The method comprises: A) introducing into a plurality of mammalian cells: a) a nucleic acid comprising a fusion polypeptide comprising: i) CRISPR-Cas effector polypeptide that, when complexed with a CRISPR-Cas guide RNA, binds, but does not cleave, a target nucleic acid in the mammalian cell; and ii) a transcriptional activator polypeptide; b) a library of CRISPR-Cas guide RNAs, or a nucleic acid comprising a nucleotide sequence encoding the library of CRISPR-Cas guide RNAs, thereby producing a plurality of CRISPR-Cas effector polypeptide/guide RNA-modified cells; B) introducing into the CRISPR-Cas effector polypeptide/guide RNA-modified cells a viral genome and a nucleic acid comprising a nucleotide sequence encoding helper functions for packaging the viral genome into a viral virion, thereby producing a plurality of packaging cells; and C) determining the number of virions produced by the packaging cell. An increase in virion production by an individual packaging cell in the plurality of packaging cells, compared to the level of virion production by a control mammalian cell not modified with the guide RNA introduced into the individual packaging cell, indicates that the gene product encoded by the target of the guide RNA, when overexpressed, enhances production of the virus by the cell. In some cases, the transcriptional activator polypeptide is a VP64 polypeptide.

Suitable the CRISPR-Cas effector polypeptides are known to those skilled in the art and include, e.g., a Cas9 polypeptide.

In some cases, the guide RNAs present in the library of guide RNAs comprise a protein-binding RNA aptamer. In some cases, the aptamer is capable of binding an adaptor protein. In some cases, the adaptor protein comprises a bacteriophage coat protein. For example, a suitable bacteriophage coat protein comprises an MS2 polypeptide. As an example, the adaptor protein can be an MS2-P65-HSF1 fusion polypeptide. In some cases, the mammalian cell line is genetically modified with a nucleic acid comprising a nucleotide sequence encoding the adaptor protein.

A method of the present disclosure can further comprise sequencing the nucleic acid encoding the identified gene product.

Methods of Identifying Genes that, when Knocked Out, Provide for Increased Production of AAV Virions The present disclosure provides a method of identifying a gene product that when knocked out, enhances production of a virus by a mammalian cell. The method comprises: A) introducing into a plurality of mammalian cells: a) a CRISPR-Cas effector polypeptide or a nucleic acid comprising a nucleotide sequence encoding the CRISPR-Cas effector polypeptide; b) a library of CRISPR-Cas guide RNAs, or a nucleic acid comprising a nucleotide sequence encoding the library of CRISPR-Cas guide RNAs, thereby producing a plurality of CRISPR-Cas effector polypeptide/ guide RNA-modified cells; B) introducing into the CRISPR-Cas effector polypeptide/guide RNA-modified cells a viral genome and a nucleic acid comprising a nucleotide sequence encoding helper functions for packaging the viral genome into a viral virion, thereby producing a plurality of packaging cells; and C) determining the number of virions produced by the packaging cell. A decrease in virion production by an individual packaging cell in the plurality of packaging cells, compared to the level of virion production by a control mammalian cell not modified with the guide RNA introduced into the individual packaging cell, indicates that the gene product encoded by the target of the guide RNA, when knocked out, enhances production of the virus by the cell. A method of the present disclosure can further comprise sequencing the nucleic acid encoding the identified gene product.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-42 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. An in vitro mammalian cell comprising one or more genetic modifications that provide for increased adeno-associated virus (AAV) virion production by the cell.

Aspect 2. The mammalian cell of aspect 1, wherein the genetic modification results in decreased production in the cell of a gene product encoded by a coding region.

Aspect 3. The mammalian cell of aspect 2, wherein the genetic modification comprises a deletion of all or a portion of the coding region.

Aspect 4. The mammalian cell of aspect 2, wherein the genetic modification comprises insertion of one or more nucleotides such that the coding region is out of frame.

Aspect 5. The mammalian cell of aspect 1, wherein the genetic modification results in increased production of a polypeptide compared to a control mammalian cell not comprising the one or more genetic modifications.

Aspect 6. The mammalian cell of aspect 1, comprising two or more genetic modifications, wherein the two or more genetic modifications provide for:
  a) decreased production in the cell of one or more gene products encoded by the at least one coding region; and/or
  b) increased production of one or more polypeptides compared to a control mammalian cell not comprising the one or more genetic modifications.

Aspect 7. The mammalian cell of any one of aspects 1, 5, or 6, wherein the one or more genetic modifications provides for increased production of one or more polypeptides selected from: a Spindle and Kinetochore Associated Complex subunit 2 (SKA2) polypeptide; an Inositol Tri-Phosphate Receptor Interacting Protein (ITPRIP2) polypeptide; a CUGBP, Elav-like family member 2 (CELF2) polypeptide; a centrosomal protein 128 (CEP128) polypeptide, a protocadherin alpha 2 (PCDHA2) polypeptide; and an acetylcholinesterase (Cartwright blood group) (ACHE) polypeptide.

Aspect 8. The mammalian cell of any one of aspects 1-4 or 6, wherein the one or more genetic modifications provides for reduced production of one or more gene products selected from: an endoplasmic reticulum lectin 1 polypeptide; a kinesin-like protein KIF23 polypeptide; an interferon-induced protein with tetratricopeptide repeats 5 polypeptide; a caspase recruitment domain-containing protein 8 polypeptide; and a mir-4770 nucleic acid.

Aspect 9. The mammalian cell of aspect 1, wherein the one or more genetic modifications provides for increased production of:
  a) a Spindle and Kinetochore Associated Complex subunit 2 (SKA2) polypeptide; or
  b) an Inositol Tri-Phosphate Receptor Interacting Protein (ITPRIP2) polypeptide; or
  c) both a SKA2 polypeptide and an ITPRIP2 polypeptide, compared to a control mammalian cell not comprising the one or more genetic modifications.

Aspect 10. The mammalian cell of aspect 9, wherein the genetic modification comprises integration into the genome of the cell of a nucleic acid comprising a nucleotide sequence encoding the SKA2 polypeptide and/or the ITPRIP2 polypeptide.

Aspect 11. The mammalian cell of aspect 10, wherein the nucleotide sequence is operably linked to a heterologous transcriptional control element.

Aspect 12. The mammalian cell of aspect 11, wherein the heterologous transcriptional control element is a regulatable promoter.

Aspect 13. The mammalian cell of aspect 12, wherein the regulatable promoter is an inducible promoter.

Aspect 14. The mammalian cell of aspect 12, wherein the regulatable promoter is a repressible promoter.

Aspect 15. The mammalian cell of any one of aspects 9-14, wherein the SKA2 polypeptide and/or the ITPRIP2 polypeptide are produced at a level that is at least 25% higher than the level of the SKA2 polypeptide and/or the ITPRIP2 polypeptide in a control cell.

Aspect 16. The mammalian cell of any one of aspects 9-14, wherein the SKA2 polypeptide and/or the ITPRIP2 polypeptide are produced at a level that is at least 2-fold higher than the level of the SKA2 polypeptide and/or the ITPRIP2 polypeptide in a control cell.

Aspect 17. The mammalian cell of any one of aspects 9-14, wherein the SKA2 polypeptide and/or the ITPRIP2 polypeptide are produced at a level that is at least 10-fold higher than the level of the SKA2 polypeptide and/or the ITPRIP2 polypeptide in a control cell.

Aspect 18. The mammalian cell of any one of aspects 9-14, wherein the SKA2 polypeptide and/or the ITPRIP2 polypeptide are produced at a level that is at least 50-fold higher than the level of the SKA2 polypeptide and/or the ITPRIP2 polypeptide in a control cell.

Aspect 19. The mammalian cell of any one of aspects 9-14, wherein the SKA2 polypeptide comprises an amino acid sequence having at least 85% amino acid sequence identity to:

```
                              (SEQ ID NO: 1)
MASEVGHNLE SPETPGGGGW TRVEFPPPAP KGAATVWCLN

RLGSRKLSLI WITFNTGWNM KSRLIILIQQ VSCHH.
```

Aspect 20. The mammalian cell of any one of aspects 9-14, wherein the ITPRIP2 polypeptide comprises an amino acid sequence having at least 85% amino acid sequence identity to the amino acid sequence depicted in FIG. 6.

Aspect 21. The mammalian cell of any one of aspects 1-20, comprising an adeno-associated virus (AAV) genome.

Aspect 22. The mammalian cell of aspect 21, wherein the AAV genome is a recombinant AAV genome comprising a heterologous nucleic acid encoding one or more heterologous gene products.

Aspect 23. The mammalian cell of aspect 22, wherein the one or more heterologous gene products comprises a polynucleotide.

Aspect 24. The mammalian cell of aspect 22, wherein the one or more heterologous gene products comprises a polypeptide.

Aspect 25. The mammalian cell of any one of aspects 21-24, wherein the cell, when provided with helper functions, packages the AAV genome into an AAV virion, and produces the AAV virion at a level that is higher than the level of AAV virion produced by a control cell.

Aspect 26. The mammalian cell of aspect 25, wherein the AAV virion is produced at a level that is at least 1.5 times higher than the level of AAV virion produced by a control cell.

Aspect 27. The mammalian cell of aspect 25, wherein the AAV virion is produced at a level that is at least 2 times higher than the level of AAV virion produced by a control cell.

Aspect 28. A method of producing an AAV virion, the method comprising:

a) culturing the mammalian cell of any one of aspects 21-27 in vitro in a liquid culture medium such that the mammalian cell produces the AAV virion; and b) harvesting the AAV virion from the culture medium.

Aspect 29. The method of aspect 28, comprising purifying the AAV virion from the culture medium.

Aspect 30. The method of aspect 28 or aspect 29, wherein the AAV virion is a recombinant AAV virion comprising a heterologous nucleic acid encoding one or more heterologous gene products.

Aspect 31. The method of aspect 30, wherein the one or more heterologous gene products comprises a polynucleotide.

Aspect 32. The method of aspect 28, wherein the one or more heterologous gene products comprises a polypeptide.

Aspect 33. A method of identifying a gene product that, when overexpressed, enhances production of a virus by a mammalian cell, the method comprising:

A) introducing into a plurality of mammalian cells:

a) a nucleic acid comprising a fusion polypeptide comprising: i) CRISPR-Cas effector polypeptide that, when complexed with a CRISPR-Cas guide RNA, binds, but does not cleave, a target nucleic acid in the mammalian cell; and ii) a transcriptional activator polypeptide;

b) a library of CRISPR-Cas guide RNAs, or a nucleic acid comprising a nucleotide sequence encoding the library of CRISPR-Cas guide RNAs, thereby producing a plurality of CRISPR-Cas effector polypeptide/guide RNA-modified cells;

B) introducing into the CRISPR-Cas effector polypeptide/guide RNA-modified cells a viral genome and a nucleic acid comprising a nucleotide sequence encoding helper functions for packaging the viral genome into a viral virion, thereby producing a plurality of packaging cells; and C) determining the number of virions produced by the packaging cell, wherein an increase in virion production by an individual packaging cell in the plurality of packaging cells, compared to the level of virion production by a control mammalian cell not modified with the guide RNA introduced into the individual packaging cell, indicates that the gene product encoded by the target of the guide RNA, when overexpressed, enhances production of the virus by the cell.

Aspect 34. The method of aspect 33, wherein the guide RNAs present in the library of guide RNAs comprise a protein-binding RNA aptamer.

Aspect 35. The method of aspect 34, wherein the aptamer is capable of binding an adaptor protein.

Aspect 36. The method of aspect 35, wherein the adaptor protein comprises a bacteriophage coat protein.

Aspect 37. The method of aspect 36, wherein the bacteriophage coat protein comprises an MS2 polypeptide.

Aspect 38. The method of aspect 37, wherein the adaptor protein is an MS2-P65-HSF1 fusion polypeptide.

Aspect 39. The method of any one of aspects 35-38, wherein the mammalian cell line is genetically modified with a nucleic acid comprising a nucleotide sequence encoding the adaptor protein.

Aspect 40. The method of any one of aspects 33-39, wherein the transcriptional activator polypeptide is a VP64 polypeptide.

Aspect 41. The method of any one of aspects 33-40, comprising sequencing the nucleic acid encoding the identified gene product.

Aspect 42. A method of identifying a gene product that, when knocked out, enhances production of a virus by a mammalian cell, the method comprising:

A) introducing into a plurality of mammalian cells:

a) a CRISPR-Cas effector polypeptide or a nucleic acid comprising a nucleotide sequence encoding the CRISPR-Cas effector polypeptide;

b) a library of CRISPR-Cas guide RNAs, or a nucleic acid comprising a nucleotide sequence encoding the library of CRISPR-Cas guide RNAs, thereby producing a plurality of CRISPR-Cas effector polypeptide/guide RNA-modified cells;

B) introducing into the CRISPR-Cas effector polypeptide/guide RNA-modified cells a viral genome and a nucleic acid comprising a nucleotide sequence encoding helper functions for packaging the viral genome into a viral virion, thereby producing a plurality of packaging cells; and C) determining the number of virions produced by the packaging cell, wherein a decrease in virion production by an individual packaging cell in the plurality of packaging cells, compared to the level of virion production by a control mammalian cell not modified with the guide RNA introduced into the individual packaging cell, indicates that the gene product encoded by the target of the guide RNA, when knocked out, enhances production of the virus by the cell.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or see, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Human Embryonic Kidney (HEK) cells are one of the primary methods of AAV production. Cells are transfected with three separate plasmids that contain all of the necessary DNA produce and assemble the proteins and DNA for a viable AAV capsid. Given that HEK cells (a highly transformed cell line) have not ever been a natural target of this parvovirus infection, these cells could be genetically modified to increase their ability to make virus. To do this, a genome wide screen of the Genomic CRISPR Knock-Out (GeCKO) or Synergistic Activation Mediator (SAM) was used to either knock-out or over-express every gene in the human genome using a CRISPR/Cas9 system. The method is depicted schematically in FIG. 1. FIG. 1 presents schematic depictions of an iterative AAV manufacturing enhancement process through genetic manipulation via either over-expression mediated by dCas9-VP64 (left panel) or genetic knock-out via Cas9 (right panel).

This method focuses on iteratively altering the genetic profile of a cell and then using that altered cell to make virus to select for genetic modifications that enhance virus production. AAV was packaged, such that the AAV contained a library of guide RNAs (gRNAs) to modify genes either via a Cas9 to knock-out genes or a dCas9-VP64 to over-express genes. The AAV-delivered DNA was present as an episome in the nucleus and encoded the gRNAs used to modify the genes. After infection and genetic modification, the episome was then repackaged into virus in the modified cells, and cells with beneficial genetic modifications produced more virus. This means that virus containing the beneficial gRNA was more populous in the overall viral population. The newly packaged virus was used to infect a new batch of cells containing either Cas9 or dCas9-VP64. By iteratively packaging virus, the gRNA responsible for the increased titer became an increasingly greater percentage of the overall virus collected after each round. Eventually over multiple rounds, this library of gRNAs reached a consensus and provided targets for modification to create cell lines that produced AAV at higher titers than in unmodified HEK cells.

Expression constructs were made that contained a U6 promoter followed by a library of guide RNAs as well as an expression cassette for GFP flanked by two ITRs. The expression constructs were then packaged into rAAV2 through the standard triple transfection technique. Two guide RNA libraries were used. In one guide RNA library, each of the guide RNAs binds upstream of a target gene and recruits a transactivator, such that the target gene is activated and the encoded gene product overexpressed. The second guide RNA library included guide RNAs that target and knock out genes.

HEK293 Ts were made that expressed either: enzymatically active Cas9; or dCas9-VP64 with MS2-P65-HSF1. These cells were first infected at a range of multiplicities of infection (MOI) to find the MOI that ensured that each cell contained at least one guide RNA, as measured by green fluorescent protein (GFP) expression. An MOI of 500 was found to be best in a 24-well dish format. Cells were then given 48 hours to ensure onset of guide activation and change in gene expression.

Once gene expression had been given time to take effect, such that the Cas9 or dCas9-VP64 was produced, the cells were then transfected with the rAAV2 libraries and helper plasmid.

The episome containing the gRNA responsible for guide expression serves as a third plasmid and can be repackaged in the presence of rAAV2 and the helper plasmid. The episome was repackaged into virus and where some cells had altered genetic profiles that enhanced virus production and thus had a larger viral load. Those viruses were harvested and quantified before re-infecting 293 Ts expressing Cas9 or dCas9-VP64 at an MOI of 500. The procedure was done 4 times for the KO library and 5 times for the overexpression library before genomes were recovered and the guides were re-cloned and repackaged in wildtype 293 Ts. The process was then repeated 3 more times for each library and deep sequencing was done to quantify the fold increase of guide present as compared to the original amount of guide.

The results are shown in FIG. 2 through FIG. 5.

FIG. 2A-2D depict: A) the top hits from the GeCKO selection ranked in descending order; B) the top hits from the SAM selection ranked in descending order; C) fold increase of hits increased by over 1500-fold and the corresponding gene; D) quantification of viral genomes per mL (vg/mL) and fold increase over AAV2 production in wild-type HEK293 Ts of cells constitutively expressing the guide RNA linked to increased AAV manufacturing capability.

Figures 3A, 3B:
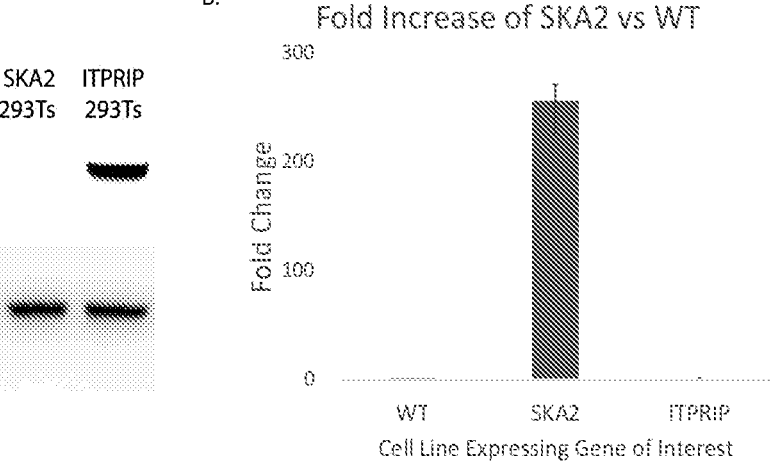
FIG. 3A-3B depict: A) Western blot confirming elevated expression of ITPRIP protein in the cell line associated with increased titer due to ITPRIP expression; B) qRT-PCR confirming overexpression of SKA2 in the cell line associated with increased titer due to SKA2 expression.
Figures 4A, 4B, 4C, 4D:
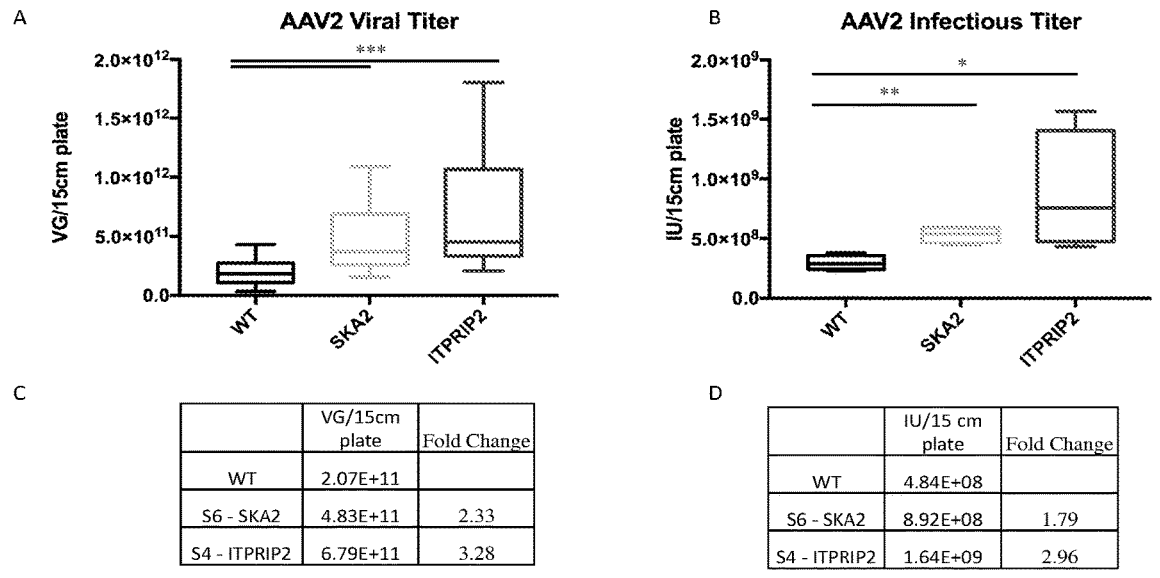
FIG. 4A-4D depict: A) Box plot showing viral titers in viral genomes (VG) per 15 mL plate of AAV2 as quantified by qPCR; B) Box plot showing infectious units (IU) per 15 mL plate as quantified by GFP expressing cells relative to total cells; C) Average viral titers per 15 mL plate as well as the fold increase relative to the WT 293T condition; D) Average infectious titers per 15 mL plate as well as the fold increase relative to the WT 293T condition.
Figures 5A, 5B, 5C, 5D:
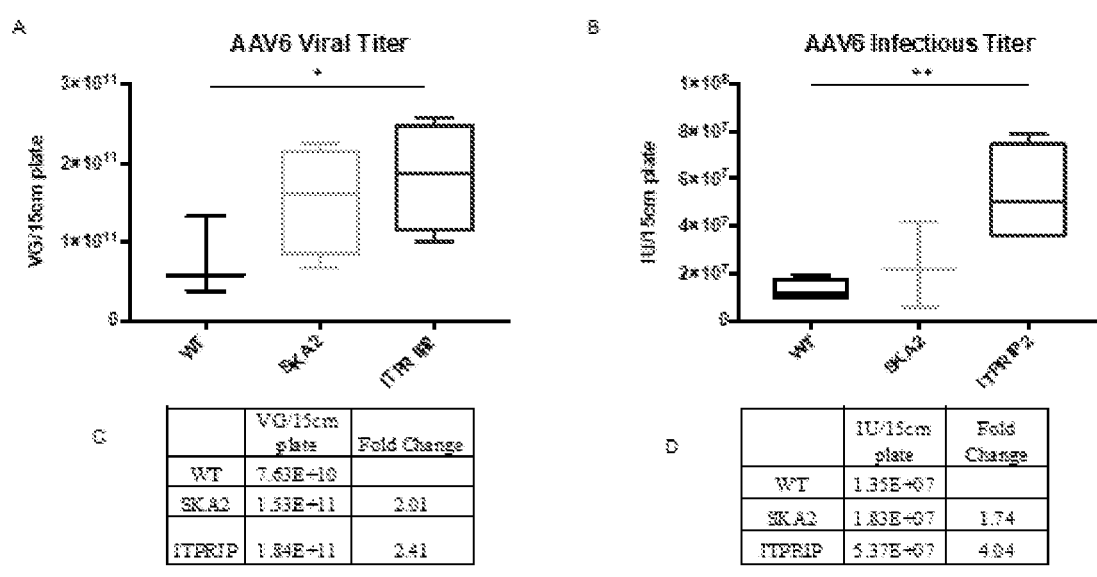
FIG. 5A-5D depict: A) Box plot showing viral titers in viral genomes (VG) per 15 mL plate of AAV6 as quantified by qPCR; B) Box plot showing infectious units (IU) per 15 mL plate of AAV6 as quantified by GFP expressing cells relative to total cells; C) Average viral titers per 15 mL plate as well as the fold increase relative to the WT 293T condition; D) Average infectious titers per 15 mL plate as well as the fold increase relative to the WT 293T condition.

FIG. 3A-3B depict: A) Western blot confirming elevated expression of ITPRIP protein in the cell line associated with increased titer due to ITPRIP expression; B) quantitative reverse transcription-polymerase chain reaction (qRT-PCR) confirming overexpression of SKA2 in the cell line associated with increased titer due to SKA2 expression.

FIG. 4A-4D depict: A) Box plot showing viral titers in viral genomes (VG) per 15 mL plate of AAV2 as quantified by qPCR; B) Box plot showing infectious units (IU) per 15 mL plate as quantified by GFP expressing cells relative to total cells; C) Average viral titers per 15 mL plate as well as the fold increase relative to the WT 293T condition; D) Average infectious titers per 15 mL plate as well as the fold increase relative to the WT 293T condition.

FIG. 5A-5D depict: A) Box plot showing viral titers in viral genomes (VG) per 15 mL plate of AAV6 as quantified by qPCR; B) Box plot showing infectious units (IU) per 15 mL plate of AAV6 as quantified by GFP expressing cells relative to total cells; C) Average viral titers per 15 mL plate as well as the fold increase relative to the WT 293T condition; D) Average infectious titers per 15 mL plate as well as the fold increase relative to the WT 293T condition.

Example 2

HEK293T cells were modified to express: i) SKA2; ii) ITPRIP; or iii) both SKA2 and ITPRIP ("dual"). The effect on AAV2 and AAV6 production was assessed. The data are presented in FIG. 16-20.

FIG. 16 shows AAV2 (upper panel) and AAV6 (lower panel) viral genome fold increase with each round normal-ized to the wild-type (WT) 293 Ts value for that round from SKA2 and ITPRIP expressing cells. Significance is based on Dunnett's multiple comparisons test where *$p \leq 0.05$, $p \leq 0.005$, *$p \leq 0.0005$. $n \geq 6$.

FIG. 17 shows AAV2 (upper panel) and AAV6 (lower panel) viral genome fold increase with each round normal-ized to the WT 293 Ts value for that round. A cell line expressing both genes of interest ("Dual") exhibited a 3.8-fold increase in packaging AAV2 and 3.5-fold in packaging AAV6. * $p \leq 0.05$, *$p \leq 0.005$, **$p \leq 0.0005$ $n \geq 4$.

Figure 18:
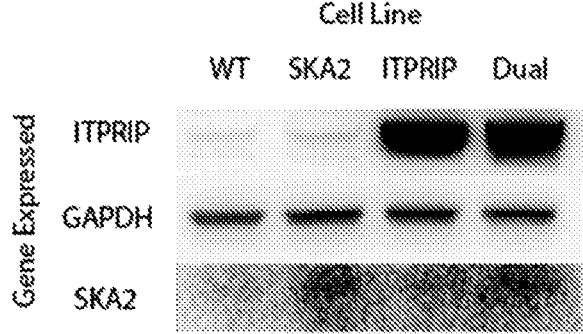
FIG. 18 depicts Western blot analysis of: i) SKA2 production in a cell line expressing SKA2 and in a 'dual' cell line expressing both SKA2 and ITPRIP; and ii) ITPRIP production in an ITPRIP expressing cell line and in a 'dual' cell line expressing both SKA2 and ITPRIP.

As shown in FIG. 18, Western blot analysis confirmed upregulation of SKA2 in a cell line expressing SKA2 and in a 'dual' cell line expressing both SKA2 and ITPRIP as well as upregulation of ITPRIP in an ITPRIP expressing cell line and in a 'dual' cell line expressing both SKA2 and ITPRIP.

FIG. 19 presents Table 1: Compiled AAV2 viral titers from WT 293 Ts as well as 293 Ts induced to express: i) SKA2; ii) ITPRIP; or iii) both SKA2 and ITPRIP simulta-neously ("dual")

FIG. 20 presents Table 2: Compiled AAV6 viral titers from WT 293 Ts as well as 293 Ts induced to express: i) SKA2; ii) ITPRIP; or iii) both SKA2 and ITPRIP simulta-neously ("dual").

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, pro-cess, process step or steps, to the objective, spirit and scope of the present invention. All such modifications are intended to be within the scope of the claims appended hereto.

---

What is claimed is:

1. An in vitro mammalian cell comprising:

(i) one or more genetic modifications that provide for increased adeno-associated virus (AAV) virion production by the cell, wherein the genetic modification comprises:

integration into the genome of the cell of a nucleic acid comprising a nucleotide sequence encoding the Spindle and Kinetochore Associated Complex subunit 2 (SKA2) polypeptide and/or the Inositol Tri-Phosphate Receptor Interacting Protein (ITPRIP2) polypeptide and results in increased production of the SKA2 polypeptide and/or the ITPRIP2 polypeptide, respectively, compared to a control mammalian cell not comprising the one or more genetic modifications; and (ii) a recombinant adeno-associated virus (AAV) genome comprising a heterologous nucleic acid encoding one or more heterologous gene products, wherein the cell, when provided with helper functions, packages the AAV genome into an AAV virion, and produces the AAV virion at a level that is higher than the level of AAV virion produced by a control cell.

2. The in vitro mammalian cell of claim 1, wherein the one or more genetic modifications provides for increased production of:

both the SKA2 polypeptide and the ITPRIP2 polypeptide, compared to a control mammalian cell not comprising the one or more genetic modifications.

3. The in vitro mammalian cell of claim 2, wherein the genetic modification comprises integration into the genome of the cell of a nucleic acid comprising a nucleotide sequence encoding the SKA2 polypeptide and a nucleic acid comprising a nucleotide sequence encoding the ITPRIP2 polypeptide.

4. The in vitro mammalian cell of claim 1, wherein the nucleotide sequence is operably linked to a heterologous transcriptional control element.

5. A method of producing an AAV virion, the method comprising:

a) culturing the mammalian cell of claim 1 in vitro in a liquid culture medium such that the mammalian cell produces the AAV virion; and b) harvesting the AAV virion from the culture medium.

6. The in vitro mammalian cell of claim 1, wherein the one or more genetic modifications comprises integration into the genome of the cell of a nucleic acid comprising a nucleotide sequence encoding the SKA2 polypeptide and results in increased production of the SKA2 polypeptide.

7. The in vitro mammalian cell of claim 6, wherein the nucleotide sequence is operably linked to a heterologous transcriptional control element.

8. The in vitro mammalian cell of claim 1, wherein the one or more genetic modifications comprises integration into the genome of the cell of a nucleic acid comprising a nucleotide sequence encoding the ITPRIP2 polypeptide and results in increased production of the ITPRIP2 polypeptide.

9. The in vitro mammalian cell of claim 8, wherein the nucleotide sequence is operably linked to a heterologous transcriptional control element.

10. The in vitro mammalian cell of claim 3, wherein the nucleotide sequence encoding the SKA2 polypeptide is operably linked to a heterologous transcriptional control element and the nucleotide sequence encoding the ITPRIP2 polypeptide is operably linked to a heterologous transcriptional control element.

* * * * *

SEQUENCE LISTING

```
<160> NUMBER OF SEQ ID NOS: 12

<210> SEQ ID NO 1
<211> LENGTH: 75
<212> TYPE: PRT
<213> ORGANISM: Homo sapiens

<400> SEQUENCE: 1

Met Ala Ser Glu Val Gly His Asn Leu Glu Ser Pro Glu Thr Pro Gly
1               5                   10                  15

Gly Gly Gly Trp Thr Arg Val Glu Phe Pro Pro Pro Ala Pro Lys Gly
                20                  25                  30

Ala Ala Thr Val Trp Cys Leu Asn Arg Leu Gly Ser Arg Lys Leu Ser
            35                  40                  45

Leu Ile Trp Ile Thr Phe Asn Thr Gly Trp Asn Met Lys Ser Arg Leu
        50                  55                  60

Ile Ile Leu Ile Gln Gln Val Ser Cys His His
65                  70                  75

<210> SEQ ID NO 2
<211> LENGTH: 58
<212> TYPE: RNA
<213> ORGANISM: Artificial sequence
<220> FEATURE:
<223> OTHER INFORMATION: synthetic sequence

<400> SEQUENCE: 2
```

```
gaguuauggg gucaucuauc cuucccuugg aaaaugaucu gagaugacac uguagcuc          58

<210> SEQ ID NO 3
<211> LENGTH: 547
<212> TYPE: PRT
<213> ORGANISM: Homo sapiens

<400> SEQUENCE: 3

Met Ala Met Gly Leu Phe Arg Val Cys Leu Val Val Val Thr Ala Ile
1               5                   10                  15

Ile Asn His Pro Leu Leu Phe Pro Arg Glu Asn Ala Thr Val Pro Glu
                20                  25                  30

Asn Glu Glu Glu Ile Ile Arg Lys Met Gln Ala His Gln Glu Lys Leu
        35                  40                  45

Gln Leu Glu Gln Leu Arg Leu Glu Glu Glu Val Ala Arg Leu Ala Ala
    50                  55                  60

Glu Lys Glu Ala Leu Glu Gln Val Ala Glu Glu Gly Arg Gln Gln Asn
65                  70                  75                  80

Glu Thr Arg Val Thr Trp Asp Leu Trp Ser Thr Leu Cys Met Ile Leu
                85                  90                  95

Phe Leu Met Ile Glu Val Trp Arg Gln Asp His Gln Glu Gly Pro Ser
                100                 105                 110

Pro Glu Cys Leu Gly Gly Glu Glu Asp Glu Leu Pro Gly Leu Gly Gly
            115                 120                 125

Ala Pro Leu Gln Gly Leu Thr Leu Pro Asn Lys Ala Thr Leu Gly His
    130                 135                 140

Phe Tyr Glu Arg Cys Ile Arg Gly Ala Thr Ala Asp Ala Ala Arg Thr
145                 150                 155                 160

Arg Glu Phe Leu Glu Gly Phe Val Asp Asp Leu Leu Glu Ala Leu Arg
                165                 170                 175

Ser Leu Cys Asn Arg Asp Thr Asp Met Glu Val Glu Asp Phe Ile Gly
            180                 185                 190

Val Asp Ser Met Tyr Glu Asn Trp Gln Val Asp Arg Pro Leu Leu Cys
            195                 200                 205

His Leu Phe Val Pro Phe Thr Pro Pro Glu Pro Tyr Arg Phe His Pro
    210                 215                 220

Glu Leu Trp Cys Ser Gly Arg Ser Val Pro Leu Asp Arg Gln Gly Tyr
225                 230                 235                 240

Gly Gln Ile Lys Val Val Arg Ala Asp Gly Asp Thr Leu Ser Cys Ile
                245                 250                 255

Cys Gly Lys Thr Lys Leu Gly Glu Asp Met Leu Cys Leu Leu His Gly
            260                 265                 270

Arg Asn Ser Met Ala Pro Pro Cys Gly Asp Met Glu Asn Leu Leu Cys
            275                 280                 285

Ala Thr Asp Ser Leu Tyr Leu Asp Thr Met Gln Val Met Lys Trp Phe
    290                 295                 300

Gln Thr Ala Leu Thr Arg Ala Trp Lys Gly Ile Ala His Lys Tyr Glu
305                 310                 315                 320

Phe Asp Leu Ala Phe Gly Gln Leu Asp Ser Pro Gly Ser Leu Lys Ile
                325                 330                 335

Lys Phe Arg Ser Gly Lys Phe Met Pro Phe Asn Leu Ile Pro Val Ile
            340                 345                 350

Gln Cys Asp Asp Ser Asp Leu Tyr Phe Val Ser His Leu Pro Arg Glu
            355                 360                 365
```

-continued

```
Pro Ser Glu Gly Thr Pro Ala Ser Ser Thr Asp Trp Leu Leu Ser Phe
    370             375             380
```

```
Ala Val Tyr Glu Arg His Phe Leu Arg Thr Thr Leu Lys Ala Leu Pro
385             390             395             400
```

```
Glu Gly Ala Cys His Leu Ser Cys Leu Gln Ile Ala Ser Phe Leu Leu
                405             410             415
```

```
Ser Lys Gln Ser Arg Leu Thr Gly Pro Ser Gly Leu Ser Ser Tyr His
            420             425             430
```

```
Leu Lys Thr Ala Leu Leu His Leu Leu Leu Arg Gln Ala Ala Asp
            435             440             445
```

```
Trp Lys Ala Gly Gln Leu Asp Ala Arg Leu His Glu Leu Leu Cys Phe
    450             455             460
```

```
Leu Glu Lys Ser Leu Leu Gln Lys Lys Leu His His Phe Phe Ile Gly
465             470             475             480
```

```
Asn Arg Lys Val Pro Glu Ala Met Gly Leu Pro Glu Ala Val Leu Arg
                485             490             495
```

```
Ala Glu Pro Leu Asn Leu Phe Arg Pro Phe Val Leu Gln Arg Ser Leu
            500             505             510
```

```
Tyr Arg Lys Thr Leu Asp Ser Phe Tyr Glu Met Leu Lys Asn Ala Pro
            515             520             525
```

```
Ala Leu Ile Ser Glu Tyr Ser Leu His Val Pro Ser Asp Gln Pro Thr
    530             535             540
```

```
Pro Lys Ser
545
```

```
<210> SEQ ID NO 4
<211> LENGTH: 508
<212> TYPE: PRT
<213> ORGANISM: Homo sapiens

<400> SEQUENCE: 4
```

```
Met Arg Cys Pro Lys Ser Ala Val Thr Met Arg Asn Glu Glu Leu Leu
1               5               10              15
```

```
Leu Ser Asn Gly Thr Ala Asn Lys Met Asn Gly Ala Leu Asp His Ser
            20              25              30
```

```
Asp Gln Pro Asp Pro Asp Ala Ile Lys Met Phe Val Gly Gln Ile Pro
            35              40              45
```

```
Arg Ser Trp Ser Glu Lys Glu Leu Lys Glu Leu Phe Glu Pro Tyr Gly
    50              55              60
```

```
Ala Val Tyr Gln Ile Asn Val Leu Arg Asp Arg Ser Gln Asn Pro Pro
65              70              75              80
```

```
Gln Ser Lys Gly Cys Cys Phe Val Thr Phe Tyr Thr Arg Lys Ala Ala
                85              90              95
```

```
Leu Glu Ala Gln Asn Ala Leu His Asn Ile Lys Thr Leu Pro Gly Met
            100             105             110
```

```
His His Pro Ile Gln Met Lys Pro Ala Asp Ser Glu Lys Ser Asn Ala
        115             120             125
```

```
Val Glu Asp Arg Lys Leu Phe Ile Gly Met Val Ser Lys Lys Cys Asn
    130             135             140
```

```
Glu Asn Asp Ile Arg Val Met Phe Ser Pro Phe Gly Gln Ile Glu Glu
145             150             155             160
```

```
Cys Arg Ile Leu Arg Gly Pro Asp Gly Leu Ser Arg Gly Cys Ala Phe
                165             170             175
```

```
Val Thr Phe Ser Thr Arg Ala Met Ala Gln Asn Ala Ile Lys Ala Met
```

-continued

```
                  180             185             190
His Gln Ser Gln Thr Met Glu Gly Cys Ser Ser Pro Ile Val Val Lys
              195             200             205

Phe Ala Asp Thr Gln Lys Asp Lys Glu Gln Arg Arg Leu Gln Gln Gln
          210             215             220

Leu Ala Gln Gln Met Gln Gln Leu Asn Thr Ala Thr Trp Gly Asn Leu
225             230             235             240

Thr Gly Leu Gly Gly Leu Thr Pro Gln Tyr Leu Ala Leu Leu Gln Gln
              245             250             255

Ala Thr Ser Ser Ser Asn Leu Gly Ala Phe Ser Gly Ile Gln Gln Met
              260             265             270

Ala Gly Met Asn Ala Leu Gln Leu Gln Asn Leu Ala Thr Leu Ala Ala
          275             280             285

Ala Ala Ala Ala Ala Gln Thr Ser Ala Thr Ser Thr Asn Ala Asn Pro
          290             295             300

Leu Ser Thr Thr Ser Ser Ala Leu Gly Ala Leu Thr Ser Pro Val Ala
305             310             315             320

Ala Ser Thr Pro Asn Ser Thr Ala Gly Ala Ala Met Asn Ser Leu Thr
              325             330             335

Ser Leu Gly Thr Leu Gln Gly Leu Ala Gly Ala Thr Val Gly Leu Asn
          340             345             350

Asn Ile Asn Ala Leu Ala Gly Met Ala Ala Leu Asn Gly Gly Leu Gly
          355             360             365

Ala Thr Gly Leu Thr Asn Gly Thr Ala Gly Thr Met Asp Ala Leu Thr
          370             375             380

Gln Ala Tyr Ser Gly Ile Gln Gln Tyr Ala Ala Ala Ala Leu Pro Thr
385             390             395             400

Leu Tyr Ser Gln Ser Leu Leu Gln Gln Gln Ser Ala Ala Gly Ser Gln
              405             410             415

Lys Glu Gly Pro Glu Gly Ala Asn Leu Phe Ile Tyr His Leu Pro Gln
              420             425             430

Glu Phe Gly Asp Gln Asp Ile Leu Gln Met Phe Met Pro Phe Gly Asn
          435             440             445

Val Ile Ser Ala Lys Val Phe Ile Asp Lys Gln Thr Asn Leu Ser Lys
          450             455             460

Cys Phe Gly Phe Val Ser Tyr Asp Asn Pro Val Ser Ala Gln Ala Ala
465             470             475             480

Ile Gln Ala Met Asn Gly Phe Gln Ile Gly Met Lys Arg Leu Lys Val
              485             490             495

Gln Leu Lys Arg Ser Lys Asn Asp Ser Lys Pro Tyr
              500             505
```

<210> SEQ ID NO 5
<211> LENGTH: 1094
<212> TYPE: PRT
<213> ORGANISM: Homo sapiens

<400> SEQUENCE: 5

```
Met Ala Glu Ser Ser Ser Glu Ser Asp His Phe Arg Cys Arg Asp Arg
1               5               10              15

Leu Ser Pro Trp Ala Ala Arg Ser Thr His Arg Gly Thr Arg Ser Leu
          20              25              30

Pro Thr Val Glu Val Thr Glu Lys Val Asn Thr Ile Thr Ser Thr Leu
          35              40              45
```

-continued

```
Gln Asp Thr Ser Arg Asn Leu Arg Gln Val Asp Gln Met Leu Gly Arg
    50              55              60

Tyr Arg Glu Tyr Ser Asn Gly Gln Ala Gly Ala Ile Glu His Leu Lys
65              70              75              80

Glu Ser Leu Glu Gln Ser Ile Asp Gln Leu Arg Ser Gln Arg Leu Leu
                85              90              95

Arg Asn Ser Gly Gly Arg Ser Ile Ser Val Thr Ser Leu Ser Ala Ser
                100             105             110

Asp Leu Asp Gly Gly Thr Gly Ser Glu Leu His His Phe Pro Pro Thr
            115             120             125

Ser Pro Leu Lys Asp Tyr Gly Asp Pro Gln Gly Ile Lys Arg Met Arg
    130             135             140

Ser Arg Thr Gly Val Arg Phe Val Gln Glu Thr Asp Asp Met Thr Gln
145             150             155             160

Leu His Gly Phe His Gln Ser Leu Arg Asp Leu Ser Ser Glu Gln Ile
                165             170             175

Arg Leu Gly Asp Asp Phe Asn Arg Glu Leu Ser Arg Arg Ser Arg Ser
            180             185             190

Asp Ala Glu Thr Lys Arg Ala Leu Glu Glu Leu Thr Glu Lys Leu Asn
            195             200             205

Glu Ala Gln Lys Gln Glu Val Val Ser Asp Arg Val Glu Arg Arg Leu
    210             215             220

Gln Glu Leu Glu Arg Glu Met Arg Thr Glu Arg Glu Leu Val Glu Arg
225             230             235             240

Arg Gln Asp Gln Leu Gly Leu Met Ser Leu Gln Leu Gln Glu Ala Leu
            245             250             255

Lys Lys Gln Glu Ala Lys Ala Asp Glu His Glu Gly Ala Ile Lys Asn
            260             265             270

Lys Leu Arg Gln Thr Glu Thr Glu Lys Asn Gln Leu Glu Gln Glu Leu
    275             280             285

Glu Leu Ser Arg Arg Leu Leu Asn Gln Ser Glu Gly Ser Arg Glu Thr
    290             295             300

Leu Leu His Gln Val Glu Glu Leu Arg Thr Gln Leu Thr Lys Ala Glu
305             310             315             320

Gly Asp Arg Lys Gly Leu Gln His Gln Val Ser Gln Ile Ser Lys Gln
            325             330             335

Gln Ser Asn Tyr Gln Asp Glu Gln Gly Glu Asp Trp Arg Phe Arg Arg
            340             345             350

Gly Val Glu Arg Glu Lys Gln Asp Leu Glu Lys Gln Met Ser Asp Leu
            355             360             365

Arg Val Gln Leu Asn Phe Ser Ala Met Ala Ser Glu Leu Glu Glu Val
    370             375             380

Lys Arg Cys Met Glu Arg Lys Asp Lys Glu Lys Ala His Leu Ala Ser
385             390             395             400

Gln Val Glu Asn Leu Thr Arg Glu Leu Glu Asn Gly Glu Lys Gln Gln
            405             410             415

Leu Gln Met Leu Asp Arg Leu Lys Glu Ile Gln Asn His Phe Asp Thr
            420             425             430

Cys Glu Ala Glu Arg Lys His Ala Asp Leu Gln Ile Ser Glu Leu Thr
            435             440             445

Arg His Ala Glu Asp Ala Thr Lys Gln Ala Glu Arg Tyr Leu Ser Glu
    450             455             460

Leu Gln Gln Ser Glu Ala Leu Lys Glu Glu Ala Glu Lys Arg Arg Glu
```

-continued

```
465              470              475              480

Asp Leu Lys Leu Lys Ala Gln Glu Ser Ile Arg Gln Trp Lys Leu Lys
            485              490              495

His Lys Lys Leu Glu Arg Ala Leu Glu Lys Gln Ser Glu Thr Val Asp
            500              505              510

Glu Leu Thr Gly Lys Asn Asn Gln Ile Leu Lys Glu Lys Asp Glu Leu
            515              520              525

Lys Thr Gln Leu Tyr Ala Ala Leu Gln Gln Ile Glu Asn Leu Arg Lys
            530              535              540

Glu Leu Asn Asp Val Leu Thr Lys Arg Ala Leu Gln Glu Glu Glu Leu
545              550              555              560

His Ser Lys Glu Glu Lys Leu Arg Asp Ile Lys Ser His Gln Ala Asp
            565              570              575

Leu Glu Leu Glu Val Lys Asn Ser Leu Asp Thr Ile His Arg Leu Glu
            580              585              590

Ser Glu Leu Lys Lys Gln Ser Lys Ile Gln Ser Gln Met Lys Val Glu
            595              600              605

Lys Ala His Leu Glu Glu Glu Ile Ala Glu Leu Lys Lys Ser Gln Ala
            610              615              620

Gln Asp Lys Ala Lys Leu Leu Glu Met Gln Glu Ser Ile Lys Asp Leu
625              630              635              640

Ser Ala Ile Arg Ala Asp Leu Ala Asn Lys Leu Ala Glu Glu Glu Arg
            645              650              655

Ala Lys Lys Ala Val Leu Lys Asp Leu Ser Asp Leu Thr Ala Gln Ala
            660              665              670

Lys Ser Arg Asp Glu Glu Thr Ala Thr Ile Ile Thr Gln Leu Lys Leu
            675              680              685

Glu Arg Asp Val His Gln Arg Glu Leu Lys Asp Leu Thr Ser Ser Leu
            690              695              700

Gln Ser Val Lys Thr Lys His Glu Gln Asn Ile Gln Glu Leu Met Lys
705              710              715              720

His Phe Lys Lys Glu Lys Ser Glu Ala Glu Asn His Ile Arg Thr Leu
            725              730              735

Lys Ala Glu Ser Leu Glu Glu Lys Asn Met Ala Lys Ile His Arg Gly
            740              745              750

Gln Leu Glu Lys Leu Lys Ser Gln Cys Asp Arg Leu Thr Glu Glu Leu
            755              760              765

Thr Gln Asn Glu Asn Glu Asn Lys Lys Leu Lys Leu Lys Tyr Gln Cys
            770              775              780

Leu Lys Asp Gln Leu Glu Glu Arg Glu Lys His Ile Ser Ile Glu Glu
785              790              795              800

Glu His Leu Arg Arg Met Glu Glu Ala Arg Leu Gln Leu Lys Asp Gln
            805              810              815

Leu Leu Cys Leu Glu Thr Glu Gln Glu Ser Ile Leu Gly Val Ile Gly
            820              825              830

Lys Glu Ile Asp Ala Ala Cys Lys Thr Phe Ser Lys Asp Ser Val Glu
            835              840              845

Lys Leu Lys Val Phe Ser Ser Gly Pro Asp Ile His Tyr Asp Pro His
            850              855              860

Arg Trp Leu Ala Glu Ser Lys Thr Lys Leu Gln Trp Leu Cys Glu Glu
865              870              875              880

Leu Lys Glu Arg Glu Asn Arg Glu Lys Asn Leu Arg His Gln Leu Met
            885              890              895
```

-continued

```
Leu Cys Arg Gln Gln Leu Arg Asn Leu Thr Glu Asn Lys Glu Ser Glu
            900                 905                 910

Leu Gln Cys Leu Phe Gln Gln Ile Glu Arg Gln Glu Gln Leu Leu Asp
            915                 920                 925

Glu Ile His Arg Glu Lys Arg Asp Leu Leu Glu Glu Thr Gln Arg Lys
            930                 935                 940

Asp Glu Glu Met Gly Ser Leu Gln Asp Arg Val Ile Ala Leu Glu Thr
945                 950                 955                 960

Ser Thr Gln Val Ala Leu Asp His Leu Glu Ser Val Pro Glu Lys Leu
                965                 970                 975

Ser Leu Leu Glu Asp Phe Lys Asp Phe Arg Asp Ser Cys Ser Ser Ser
                980                 985                 990

Glu Arg Thr Asp Gly Arg Tyr Ser Lys Tyr Arg Val Arg Arg Asn Ser
            995                 1000                1005

Leu Gln His His Gln Asp Asp Thr Lys Tyr Arg Thr Lys Ser Phe
    1010                1015                1020

Lys Gly Asp Arg Thr Phe Leu Glu Gly Ser His Thr Arg Gly Leu
    1025                1030                1035

Asp His Ser Ser Ser Trp Gln Asp His Ser Arg Phe Leu Ser Ser
    1040                1045                1050

Pro Arg Phe Ser Tyr Val Asn Ser Phe Thr Lys Arg Thr Val Ala
    1055                1060                1065

Pro Asp Ser Ala Ser Asn Lys Glu Asp Ala Thr Met Asn Gly Thr
    1070                1075                1080

Ser Ser Gln Pro Lys Lys Glu Glu Tyr Gly Ser
    1085                1090
```

<210> SEQ ID NO 6
<211> LENGTH: 948
<212> TYPE: PRT
<213> ORGANISM: Homo sapiens

<400> SEQUENCE: 6

```
Met Ala Ser Ser Ile Arg Arg Gly Arg Gly Ala Trp Thr Arg Leu Leu
1               5                   10                  15

Ser Leu Leu Leu Leu Ala Ala Trp Glu Val Gly Ser Gly Gln Leu Arg
                20                  25                  30

Tyr Ser Val Pro Glu Glu Ala Lys His Gly Thr Phe Val Gly Arg Ile
            35                  40                  45

Ala Gln Asp Leu Gly Leu Glu Leu Glu Glu Leu Val Pro Arg Leu Phe
    50                  55                  60

Arg Val Ala Ser Lys Arg His Gly Asp Leu Leu Glu Val Asn Leu Gln
65                  70                  75                  80

Asn Gly Ile Leu Phe Val Asn Ser Arg Ile Asp Arg Glu Glu Leu Cys
                85                  90                  95

Gly Arg Ser Ala Glu Cys Ser Ile His Val Glu Val Ile Val Asp Arg
            100                 105                 110

Pro Leu Gln Val Phe His Val Glu Val Glu Val Lys Asp Ile Asn Asp
        115                 120                 125

Asn Pro Pro Ile Phe Pro Met Thr Val Lys Thr Ile Arg Phe Pro Glu
    130                 135                 140

Ser Arg Leu Leu Asp Ser Arg Phe Pro Leu Glu Gly Ala Ser Asp Ala
145                 150                 155                 160

Asp Ile Gly Val Asn Ala Leu Leu Ser Tyr Lys Leu Ser Ser Ser Glu
```

-continued

```
                165                 170                 175
Phe Phe Phe Leu Asp Ile Gln Ala Asn Asp Glu Leu Ser Glu Ser Leu
            180                 185                 190
Ser Leu Val Leu Gly Lys Ser Leu Asp Arg Glu Glu Thr Ala Glu Val
            195                 200                 205
Asn Leu Leu Leu Val Ala Thr Asp Gly Gly Lys Pro Glu Leu Thr Gly
            210                 215                 220
Thr Val Gln Ile Leu Ile Lys Val Leu Asp Val Asn Asp Asn Glu Pro
225                 230                 235                 240
Thr Phe Ala Gln Ser Val Tyr Lys Val Lys Leu Leu Glu Asn Thr Ala
                245                 250                 255
Asn Gly Thr Leu Val Val Lys Leu Asn Ala Ser Asp Ala Asp Glu Gly
            260                 265                 270
Pro Asn Ser Glu Ile Val Tyr Ser Leu Gly Ser Asp Val Ser Ser Thr
            275                 280                 285
Ile Gln Thr Lys Phe Thr Ile Asp Pro Ile Ser Gly Glu Ile Arg Thr
            290                 295                 300
Lys Gly Lys Leu Asp Tyr Glu Glu Ala Lys Ser Tyr Glu Ile Gln Val
305                 310                 315                 320
Thr Ala Thr Asp Lys Gly Thr Pro Ser Met Ser Gly His Cys Lys Ile
                325                 330                 335
Ser Leu Lys Leu Val Asp Ile Asn Asp Asn Thr Pro Glu Val Ser Ile
            340                 345                 350
Thr Ser Leu Ser Leu Pro Ile Ser Glu Asn Ala Ser Leu Gly Thr Val
            355                 360                 365
Ile Ala Leu Ile Thr Val Ser Asp Arg Asp Ser Gly Thr Asn Gly His
            370                 375                 380
Val Thr Cys Ser Leu Thr Pro His Val Pro Phe Lys Leu Val Ser Thr
385                 390                 395                 400
Phe Lys Asn Tyr Tyr Ser Leu Val Leu Asp Ser Ala Leu Asp Arg Glu
                405                 410                 415
Ser Val Ser Ala Tyr Glu Leu Val Val Thr Ala Arg Asp Gly Gly Ser
            420                 425                 430
Pro Ser Leu Trp Ala Thr Thr Ser Val Ser Ile Glu Val Ala Asp Val
            435                 440                 445
Asn Asp Asn Ala Pro Ala Phe Ala Gln Pro Glu Tyr Thr Val Phe Val
            450                 455                 460
Lys Glu Asn Asn Pro Pro Gly Cys His Ile Phe Thr Val Ser Ala Trp
465                 470                 475                 480
Asp Ala Asp Ala Gln Glu Asn Ala Leu Val Ser Tyr Ser Leu Val Glu
                485                 490                 495
Arg Arg Val Gly Glu Arg Ala Leu Ser Ser Tyr Val Ser Val His Ala
            500                 505                 510
Glu Ser Gly Lys Val Tyr Ala Leu Gln Pro Leu Asp His Glu Glu Val
            515                 520                 525
Glu Leu Leu Gln Phe Gln Val Ser Ala Arg Asp Ala Gly Val Pro Pro
            530                 535                 540
Leu Gly Ser Asn Val Thr Leu Gln Val Phe Val Leu Asp Glu Asn Asp
545                 550                 555                 560
Asn Ala Pro Ala Leu Leu Ala Pro Arg Ala Gly Thr Ala Ala Gly Ala
                565                 570                 575
Val Ser Glu Leu Val Pro Trp Ser Val Gly Ala Gly His Val Val Ala
            580                 585                 590
```

```
Lys Val Arg Ala Val Asp Ala Asp Ser Gly Tyr Asn Ala Trp Leu Ser
    595                 600                 605

Tyr Glu Leu Gln Leu Gly Thr Gly Ser Ala Arg Ile Pro Phe Arg Val
    610                 615                 620

Gly Leu Tyr Thr Gly Glu Ile Ser Thr Thr Arg Ala Leu Asp Glu Ala
625                 630                 635                 640

Asp Ser Pro Arg His Arg Leu Leu Val Leu Val Lys Asp His Gly Glu
                645                 650                 655

Pro Ala Leu Thr Ala Thr Ala Thr Val Leu Val Ser Leu Val Glu Ser
            660                 665                 670

Gly Gln Ala Pro Lys Ala Ser Ser Arg Ala Trp Val Gly Ala Ala Gly
        675                 680                 685

Ser Glu Ala Thr Leu Val Asp Val Asn Val Tyr Leu Ile Ile Ala Ile
    690                 695                 700

Cys Ala Val Ser Ser Leu Leu Val Leu Thr Val Leu Leu Tyr Thr Ala
705                 710                 715                 720

Leu Arg Cys Ser Val Pro Pro Thr Glu Gly Ala Arg Ala Pro Gly Lys
                725                 730                 735

Pro Thr Leu Val Cys Ser Ser Ala Val Gly Ser Trp Ser Tyr Ser Gln
            740                 745                 750

Gln Arg Arg Gln Arg Val Cys Ser Gly Glu Asp Pro Pro Lys Thr Asp
        755                 760                 765

Leu Met Ala Phe Ser Pro Ser Leu Ser Gln Gly Pro Asp Ser Ala Glu
    770                 775                 780

Glu Lys Gln Leu Ser Glu Ser Glu Tyr Val Gly Lys Pro Arg Gln Pro
785                 790                 795                 800

Asn Pro Asp Trp Arg Tyr Ser Ala Ser Leu Arg Ala Gly Met His Ser
                805                 810                 815

Ser Val His Leu Glu Glu Ala Gly Ile Leu Arg Ala Gly Pro Gly Gly
            820                 825                 830

Pro Asp Gln Gln Trp Pro Thr Val Ser Ser Ala Thr Pro Glu Pro Glu
        835                 840                 845

Ala Gly Glu Val Ser Pro Pro Val Gly Ala Gly Val Asn Ser Asn Ser
    850                 855                 860

Trp Thr Phe Lys Tyr Gly Pro Gly Asn Pro Lys Gln Ser Gly Pro Gly
865                 870                 875                 880

Glu Leu Pro Asp Lys Phe Ile Ile Pro Gly Ser Pro Ala Ile Ile Ser
                885                 890                 895

Ile Arg Gln Glu Pro Thr Asn Ser Gln Ile Asp Lys Ser Asp Phe Ile
            900                 905                 910

Thr Phe Gly Lys Lys Glu Glu Thr Lys Lys Lys Lys Lys Lys Lys Lys
        915                 920                 925

Gly Asn Lys Thr Gln Glu Lys Lys Glu Lys Gly Asn Ser Thr Thr Asp
    930                 935                 940

Asn Ser Asp Gln
945
```

```
<210> SEQ ID NO 7
<211> LENGTH: 614
<212> TYPE: PRT
<213> ORGANISM: Homo sapiens

<400> SEQUENCE: 7

Met Arg Pro Pro Gln Cys Leu Leu His Thr Pro Ser Leu Ala Ser Pro
```

-continued

```
1               5               10              15

Leu Leu Leu Leu Leu Leu Trp Leu Leu Gly Gly Gly Val Gly Ala Glu
            20              25              30

Gly Arg Glu Asp Ala Glu Leu Leu Val Thr Val Arg Gly Gly Arg Leu
            35              40              45

Arg Gly Ile Arg Leu Lys Thr Pro Gly Gly Pro Val Ser Ala Phe Leu
    50              55              60

Gly Ile Pro Phe Ala Glu Pro Pro Met Gly Pro Arg Arg Phe Leu Pro
65              70              75              80

Pro Glu Pro Lys Gln Pro Trp Ser Gly Val Val Asp Ala Thr Thr Phe
            85              90              95

Gln Ser Val Cys Tyr Gln Tyr Val Asp Thr Leu Tyr Pro Gly Phe Glu
            100             105             110

Gly Thr Glu Met Trp Asn Pro Asn Arg Glu Leu Ser Glu Asp Cys Leu
            115             120             125

Tyr Leu Asn Val Trp Thr Pro Tyr Pro Arg Pro Thr Ser Pro Thr Pro
    130             135             140

Val Leu Val Trp Ile Tyr Gly Gly Gly Phe Tyr Ser Gly Ala Ser Ser
145             150             155             160

Leu Asp Val Tyr Asp Gly Arg Phe Leu Val Gln Ala Glu Arg Thr Val
            165             170             175

Leu Val Ser Met Asn Tyr Arg Val Gly Ala Phe Gly Phe Leu Ala Leu
            180             185             190

Pro Gly Ser Arg Glu Ala Pro Gly Asn Val Gly Leu Leu Asp Gln Arg
            195             200             205

Leu Ala Leu Gln Trp Val Gln Glu Asn Val Ala Ala Phe Gly Gly Asp
    210             215             220

Pro Thr Ser Val Thr Leu Phe Gly Glu Ser Ala Gly Ala Ala Ser Val
225             230             235             240

Gly Met His Leu Leu Ser Pro Pro Ser Arg Gly Leu Phe His Arg Ala
            245             250             255

Val Leu Gln Ser Gly Ala Pro Asn Gly Pro Trp Ala Thr Val Gly Met
            260             265             270

Gly Glu Ala Arg Arg Arg Ala Thr Gln Leu Ala His Leu Val Gly Cys
            275             280             285

Pro Pro Gly Gly Thr Gly Gly Asn Asp Thr Glu Leu Val Ala Cys Leu
    290             295             300

Arg Thr Arg Pro Ala Gln Val Leu Val Asn His Glu Trp His Val Leu
305             310             315             320

Pro Gln Glu Ser Val Phe Arg Phe Ser Phe Val Pro Val Val Asp Gly
            325             330             335

Asp Phe Leu Ser Asp Thr Pro Glu Ala Leu Ile Asn Ala Gly Asp Phe
            340             345             350

His Gly Leu Gln Val Leu Val Gly Val Val Lys Asp Glu Gly Ser Tyr
            355             360             365

Phe Leu Val Tyr Gly Ala Pro Gly Phe Ser Lys Asp Asn Glu Ser Leu
    370             375             380

Ile Ser Arg Ala Glu Phe Leu Ala Gly Val Arg Val Gly Val Pro Gln
385             390             395             400

Val Ser Asp Leu Ala Ala Glu Ala Val Val Leu His Tyr Thr Asp Trp
            405             410             415

Leu His Pro Glu Asp Pro Ala Arg Leu Arg Glu Ala Leu Ser Asp Val
            420             425             430
```

-continued

Val Gly Asp His Asn Val Val Cys Pro Val Ala Gln Leu Ala Gly Arg
          435                 440                 445

Leu Ala Ala Gln Gly Ala Arg Val Tyr Ala Tyr Val Phe Glu His Arg
    450                 455                 460

Ala Ser Thr Leu Ser Trp Pro Leu Trp Met Gly Val Pro His Gly Tyr
465                 470                 475                 480

Glu Ile Glu Phe Ile Phe Gly Ile Pro Leu Asp Pro Ser Arg Asn Tyr
              485                 490                 495

Thr Ala Glu Glu Lys Ile Phe Ala Gln Arg Leu Met Arg Tyr Trp Ala
          500                 505                 510

Asn Phe Ala Arg Thr Gly Asp Pro Asn Glu Pro Arg Asp Pro Lys Ala
          515                 520                 525

Pro Gln Trp Pro Pro Tyr Thr Ala Gly Ala Gln Gln Tyr Val Ser Leu
    530                 535                 540

Asp Leu Arg Pro Leu Glu Val Arg Arg Gly Leu Arg Ala Gln Ala Cys
545                 550                 555                 560

Ala Phe Trp Asn Arg Phe Leu Pro Lys Leu Leu Ser Ala Thr Asp Thr
              565                 570                 575

Leu Asp Glu Ala Glu Arg Gln Trp Lys Ala Glu Phe His Arg Trp Ser
          580                 585                 590

Ser Tyr Met Val His Trp Lys Asn Gln Phe Asp His Tyr Ser Lys Gln
          595                 600                 605

Asp Arg Cys Ser Asp Leu
    610

<210> SEQ ID NO 8
<211> LENGTH: 483
<212> TYPE: PRT
<213> ORGANISM: Homo sapiens

<400> SEQUENCE: 8

Met Glu Glu Gly Gly Gly Gly Val Arg Ser Leu Val Pro Gly Gly Pro
1                   5                   10                  15

Val Leu Leu Val Leu Cys Gly Leu Leu Glu Ala Ser Gly Gly Gly Arg
              20                  25                  30

Ala Leu Pro Gln Leu Ser Asp Asp Ile Pro Phe Arg Val Asn Trp Pro
          35                  40                  45

Gly Thr Glu Phe Ser Leu Pro Thr Thr Gly Val Leu Tyr Lys Glu Asp
    50                  55                  60

Asn Tyr Val Ile Met Thr Thr Ala His Lys Glu Lys Tyr Lys Cys Ile
65                  70                  75                  80

Leu Pro Leu Val Thr Ser Gly Asp Glu Glu Glu Lys Asp Tyr Lys
              85                  90                  95

Gly Pro Asn Pro Arg Glu Leu Leu Glu Pro Leu Phe Lys Gln Ser Ser
          100                 105                 110

Cys Ser Tyr Arg Ile Glu Ser Tyr Trp Thr Tyr Glu Val Cys His Gly
          115                 120                 125

Lys His Ile Arg Gln Tyr His Glu Glu Lys Glu Thr Gly Gln Lys Ile
    130                 135                 140

Asn Ile His Glu Tyr Tyr Leu Gly Asn Met Leu Ala Lys Asn Leu Leu
145                 150                 155                 160

Phe Glu Lys Glu Arg Glu Ala Glu Glu Lys Glu Lys Ser Asn Glu Ile
              165                 170                 175

Pro Thr Lys Asn Ile Glu Gly Gln Met Thr Pro Tyr Tyr Pro Val Gly

-continued

```
                 180               185                190

Met Gly Asn Gly Thr Pro Cys Ser Leu Lys Gln Asn Arg Pro Arg Ser
            195               200               205

Ser Thr Val Met Tyr Ile Cys His Pro Glu Ser Lys His Glu Ile Leu
        210               215               220

Ser Val Ala Glu Val Thr Thr Cys Glu Tyr Glu Val Val Ile Leu Thr
225               230               235               240

Pro Leu Leu Cys Ser His Pro Lys Tyr Arg Phe Arg Ala Ser Pro Val
            245               250               255

Asn Asp Ile Phe Cys Gln Ser Leu Pro Gly Ser Pro Phe Lys Pro Leu
            260               265               270

Thr Leu Arg Gln Leu Glu Gln Gln Glu Glu Ile Leu Arg Val Pro Phe
        275               280               285

Arg Arg Asn Lys Glu Glu Asp Leu Gln Ser Thr Lys Glu Glu Arg Phe
        290               295               300

Pro Ala Ile His Lys Ser Ile Ala Ile Gly Ser Gln Pro Val Leu Thr
305               310               315               320

Val Gly Thr Thr His Ile Ser Lys Leu Thr Asp Asp Gln Leu Ile Lys
            325               330               335

Glu Phe Leu Ser Gly Ser Tyr Cys Phe Arg Gly Gly Val Gly Trp Trp
            340               345               350

Lys Tyr Glu Phe Cys Tyr Gly Lys His Val His Gln Tyr His Glu Asp
        355               360               365

Lys Asp Ser Gly Lys Thr Ser Val Val Val Gly Thr Trp Asn Gln Glu
        370               375               380

Glu His Ile Glu Trp Ala Lys Lys Asn Thr Ala Arg Ala Tyr His Leu
385               390               395               400

Gln Asp Asp Gly Thr Gln Thr Val Arg Met Val Ser His Phe Tyr Gly
            405               410               415

Asn Gly Asp Ile Cys Asp Ile Thr Asp Lys Pro Arg Gln Val Thr Val
            420               425               430

Lys Leu Lys Cys Lys Glu Ser Asp Ser Pro His Ala Val Thr Val Tyr
        435               440               445

Met Leu Glu Pro His Ser Cys Gln Tyr Ile Leu Gly Val Glu Ser Pro
        450               455               460

Val Ile Cys Lys Ile Leu Asp Thr Ala Asp Glu Asn Gly Leu Leu Ser
465               470               475               480

Leu Pro Asn

<210> SEQ ID NO 9
<211> LENGTH: 960
<212> TYPE: PRT
<213> ORGANISM: Homo sapiens

<400> SEQUENCE: 9

Met Lys Ser Ala Arg Ala Lys Thr Pro Arg Lys Pro Thr Val Lys Lys
1               5                 10                15

Gly Ser Gln Thr Asn Leu Lys Asp Pro Val Gly Val Tyr Cys Arg Val
            20                25                30

Arg Pro Leu Gly Phe Pro Asp Gln Glu Cys Cys Ile Glu Val Ile Asn
        35                40                45

Asn Thr Thr Val Gln Leu His Thr Pro Glu Gly Tyr Arg Leu Asn Arg
        50                55                60

Asn Gly Asp Tyr Lys Glu Thr Gln Tyr Ser Phe Lys Gln Val Phe Gly
```

-continued

```
65                    70                    75                    80

Thr His Thr Thr Gln Lys Glu Leu Phe Asp Val Val Ala Asn Pro Leu
                85                    90                    95

Val Asn Asp Leu Ile His Gly Lys Asn Gly Leu Leu Phe Thr Tyr Gly
                100                   105                   110

Val Thr Gly Ser Gly Lys Thr His Thr Met Thr Gly Ser Pro Gly Glu
                115                   120                   125

Gly Gly Leu Leu Pro Arg Cys Leu Asp Met Ile Phe Asn Ser Ile Gly
        130                   135                   140

Ser Phe Gln Ala Lys Arg Tyr Val Phe Lys Ser Asn Asp Arg Asn Ser
145                   150                   155                   160

Met Asp Ile Gln Cys Glu Val Asp Ala Leu Leu Glu Arg Gln Lys Arg
                165                   170                   175

Glu Ala Met Pro Asn Pro Lys Thr Ser Ser Ser Lys Arg Gln Val Asp
                180                   185                   190

Pro Glu Phe Ala Asp Met Ile Thr Val Gln Glu Phe Cys Lys Ala Glu
                195                   200                   205

Glu Val Asp Glu Asp Ser Val Tyr Gly Val Phe Val Ser Tyr Ile Glu
        210                   215                   220

Ile Tyr Asn Asn Tyr Ile Tyr Asp Leu Leu Glu Glu Val Pro Phe Asp
225                   230                   235                   240

Pro Ile Lys Pro Lys Pro Pro Gln Ser Lys Leu Leu Arg Glu Asp Lys
                245                   250                   255

Asn His Asn Met Tyr Val Ala Gly Cys Thr Glu Val Glu Val Lys Ser
                260                   265                   270

Thr Glu Glu Ala Phe Glu Val Phe Trp Arg Gly Gln Lys Lys Arg Arg
        275                   280                   285

Ile Ala Asn Thr His Leu Asn Arg Glu Ser Ser Arg Ser His Ser Val
        290                   295                   300

Phe Asn Ile Lys Leu Val Gln Ala Pro Leu Asp Ala Asp Gly Asp Asn
305                   310                   315                   320

Val Leu Gln Glu Lys Glu Gln Ile Thr Ile Ser Gln Leu Ser Leu Val
                325                   330                   335

Asp Leu Ala Gly Ser Glu Arg Thr Asn Arg Thr Arg Ala Glu Gly Asn
        340                   345                   350

Arg Leu Arg Glu Ala Gly Asn Ile Asn Gln Ser Leu Met Thr Leu Arg
        355                   360                   365

Thr Cys Met Asp Val Leu Arg Glu Asn Gln Met Tyr Gly Thr Asn Lys
        370                   375                   380

Met Val Pro Tyr Arg Asp Ser Lys Leu Thr His Leu Phe Lys Asn Tyr
385                   390                   395                   400

Phe Asp Gly Glu Gly Lys Val Arg Met Ile Val Cys Val Asn Pro Lys
                405                   410                   415

Ala Glu Asp Tyr Glu Glu Asn Leu Gln Val Met Arg Phe Ala Glu Val
                420                   425                   430

Thr Gln Glu Val Glu Val Ala Arg Pro Val Asp Lys Ala Ile Cys Gly
        435                   440                   445

Leu Thr Pro Gly Arg Arg Tyr Arg Asn Gln Pro Arg Gly Pro Val Gly
        450                   455                   460

Asn Glu Pro Leu Val Thr Asp Val Val Leu Gln Ser Phe Pro Pro Leu
465                   470                   475                   480

Pro Ser Cys Glu Ile Leu Asp Ile Asn Asp Glu Gln Thr Leu Pro Arg
                485                   490                   495
```

```
Leu Ile Glu Ala Leu Glu Lys Arg His Asn Leu Arg Gln Met Met Ile
            500                 505                 510

Asp Glu Phe Asn Lys Gln Ser Asn Ala Phe Lys Ala Leu Leu Gln Glu
            515                 520                 525

Phe Asp Asn Ala Val Leu Ser Lys Glu Asn His Met Gln Gly Lys Leu
            530                 535                 540

Asn Glu Lys Glu Lys Met Ile Ser Gly Gln Lys Leu Glu Ile Glu Arg
545                 550                 555                 560

Leu Glu Lys Lys Asn Lys Thr Leu Glu Tyr Lys Ile Glu Ile Leu Glu
                565                 570                 575

Lys Thr Thr Thr Ile Tyr Glu Glu Asp Lys Arg Asn Leu Gln Gln Glu
                580                 585                 590

Leu Glu Thr Gln Asn Gln Lys Leu Gln Arg Gln Phe Ser Asp Lys Arg
                595                 600                 605

Arg Leu Glu Ala Arg Leu Gln Gly Met Val Thr Glu Thr Thr Met Lys
            610                 615                 620

Trp Glu Lys Glu Cys Glu Arg Arg Val Ala Ala Lys Gln Leu Glu Met
625                 630                 635                 640

Gln Asn Lys Leu Trp Val Lys Asp Glu Lys Leu Lys Gln Leu Lys Ala
                645                 650                 655

Ile Val Thr Glu Pro Lys Thr Glu Lys Pro Glu Arg Pro Ser Arg Glu
                660                 665                 670

Arg Asp Arg Glu Lys Val Thr Gln Arg Ser Val Ser Pro Ser Pro Val
            675                 680                 685

Pro Leu Ser Ser Asn Tyr Ile Ala Gln Ile Ser Asn Gly Gln Gln Leu
            690                 695                 700

Met Ser Gln Pro Gln Leu His Arg Arg Ser Asn Ser Cys Ser Ser Ile
705                 710                 715                 720

Ser Val Ala Ser Cys Ile Ser Glu Trp Glu Gln Lys Ile Pro Thr Tyr
                725                 730                 735

Asn Thr Pro Leu Lys Val Thr Ser Ile Ala Arg Arg Arg Gln Gln Glu
            740                 745                 750

Pro Gly Gln Ser Lys Thr Cys Ile Val Ser Asp Arg Arg Arg Gly Met
            755                 760                 765

Tyr Trp Thr Glu Gly Arg Glu Val Val Pro Thr Phe Arg Asn Glu Ile
            770                 775                 780

Glu Ile Glu Glu Asp His Cys Gly Arg Leu Leu Phe Gln Pro Asp Gln
785                 790                 795                 800

Asn Ala Pro Pro Ile Arg Leu Arg His Arg Arg Ser Arg Ser Ala Gly
                805                 810                 815

Asp Arg Trp Val Asp His Lys Pro Ala Ser Asn Met Gln Thr Glu Thr
            820                 825                 830

Val Met Gln Pro His Val Pro His Ala Ile Thr Val Ser Val Ala Asn
            835                 840                 845

Glu Lys Ala Leu Ala Lys Cys Glu Lys Tyr Met Leu Thr His Gln Glu
            850                 855                 860

Leu Ala Ser Asp Gly Glu Ile Glu Thr Lys Leu Ile Lys Gly Asp Ile
865                 870                 875                 880

Tyr Lys Thr Arg Gly Gly Gln Ser Val Gln Phe Thr Asp Ile Glu
                885                 890                 895

Thr Leu Lys Gln Glu Ser Pro Asn Gly Ser Arg Lys Arg Arg Ser Ser
                900                 905                 910
```

-continued

```
Thr Val Ala Pro Ala Gln Pro Asp Gly Ala Glu Ser Glu Trp Thr Asp
        915                 920                 925

Val Glu Thr Arg Cys Ser Val Ala Val Glu Met Arg Ala Gly Ser Gln
        930                 935                 940

Leu Gly Pro Gly Tyr Gln His His Ala Gln Pro Lys Arg Lys Lys Pro
945                 950                 955                 960

<210> SEQ ID NO 10
<211> LENGTH: 482
<212> TYPE: PRT
<213> ORGANISM: Homo sapiens

<400> SEQUENCE: 10

Met Ser Glu Ile Arg Lys Asp Thr Leu Lys Ala Ile Leu Leu Glu Leu
1                   5                   10                  15

Glu Cys His Phe Thr Trp Asn Leu Leu Lys Glu Asp Ile Asp Leu Phe
                20                  25                  30

Glu Val Glu Asp Thr Ile Gly Gln Gln Leu Glu Phe Leu Thr Thr Lys
                35                  40                  45

Ser Arg Leu Ala Leu Tyr Asn Leu Leu Ala Tyr Val Lys His Leu Lys
        50                  55                  60

Gly Gln Asn Lys Asp Ala Leu Glu Cys Leu Glu Gln Ala Glu Glu Ile
65                  70                  75                  80

Ile Gln Gln Glu His Ser Asp Lys Glu Glu Val Arg Ser Leu Val Thr
                85                  90                  95

Trp Gly Asn Tyr Ala Trp Val Tyr Tyr His Met Asp Gln Leu Glu Glu
                100                 105                 110

Ala Gln Lys Tyr Thr Gly Lys Ile Gly Asn Val Cys Lys Lys Leu Ser
        115                 120                 125

Ser Pro Ser Asn Tyr Lys Leu Glu Cys Pro Glu Thr Asp Cys Glu Lys
        130                 135                 140

Gly Trp Ala Leu Leu Lys Phe Gly Gly Lys Tyr Tyr Gln Lys Ala Lys
145                 150                 155                 160

Ala Ala Phe Glu Lys Ala Leu Glu Val Glu Pro Asp Asn Pro Glu Phe
                165                 170                 175

Asn Ile Gly Tyr Ala Ile Thr Val Tyr Arg Leu Asp Asp Ser Asp Arg
                180                 185                 190

Glu Gly Ser Val Lys Ser Phe Ser Leu Gly Pro Leu Arg Lys Ala Val
        195                 200                 205

Thr Leu Asn Pro Asp Asn Ser Tyr Ile Lys Val Phe Leu Ala Leu Lys
        210                 215                 220

Leu Gln Asp Val His Ala Glu Ala Glu Gly Glu Lys Tyr Ile Glu Glu
225                 230                 235                 240

Ile Leu Asp Gln Ile Ser Ser Gln Pro Tyr Val Leu Arg Tyr Ala Ala
                245                 250                 255

Lys Phe Tyr Arg Arg Lys Asn Ser Trp Asn Lys Ala Leu Glu Leu Leu
                260                 265                 270

Lys Lys Ala Leu Glu Val Thr Pro Thr Ser Ser Phe Leu His His Gln
        275                 280                 285

Met Gly Leu Cys Tyr Arg Ala Gln Met Ile Gln Ile Lys Lys Ala Thr
        290                 295                 300

His Asn Arg Pro Lys Gly Lys Asp Lys Leu Lys Val Asp Glu Leu Ile
305                 310                 315                 320

Ser Ser Ala Ile Phe His Phe Lys Ala Ala Met Glu Arg Asp Ser Met
                325                 330                 335
```

-continued

```
Phe Ala Phe Ala Tyr Thr Asp Leu Ala Asn Met Tyr Ala Glu Gly Gly
            340                 345                 350

Gln Tyr Ser Asn Ala Glu Asp Ile Phe Arg Lys Ala Leu Arg Leu Glu
            355                 360                 365

Asn Ile Thr Asp Asp His Lys His Gln Ile His Tyr His Tyr Gly Arg
            370                 375                 380

Phe Gln Glu Phe His Arg Lys Ser Glu Asn Thr Ala Ile His His Tyr
385                 390                 395                 400

Leu Glu Ala Leu Lys Val Lys Asp Arg Ser Pro Leu Arg Thr Lys Leu
                405                 410                 415

Thr Ser Ala Leu Lys Lys Leu Ser Thr Lys Arg Leu Cys His Asn Ala
                420                 425                 430

Leu Asp Val Gln Ser Leu Ser Ala Leu Gly Phe Val Tyr Lys Leu Glu
                435                 440                 445

Gly Glu Lys Arg Gln Ala Ala Glu Tyr Tyr Glu Lys Ala Gln Lys Ile
            450                 455                 460

Asp Pro Glu Asn Ala Glu Phe Leu Thr Ala Leu Cys Glu Leu Arg Leu
465                 470                 475                 480

Ser Ile

<210> SEQ ID NO 11
<211> LENGTH: 537
<212> TYPE: PRT
<213> ORGANISM: Homo sapiens

<400> SEQUENCE: 11

Met Glu Lys Lys Glu Cys Pro Glu Lys Ser Ser Ser Glu Glu Glu
1               5                   10                  15

Leu Pro Arg Arg Asp Ser Gly Ser Ser Arg Asn Ile Asp Ala Ser Lys
            20                  25                  30

Leu Ile Arg Leu Gln Gly Ser Arg Lys Leu Leu Val Asp Asn Ser Ile
            35                  40                  45

Arg Glu Leu Gln Tyr Thr Lys Thr Gly Ile Phe Phe Gln Ala Glu Ala
        50                  55                  60

Cys Val Thr Asn Asp Thr Val Tyr Arg Glu Leu Pro Cys Val Ser Glu
65                  70                  75                  80

Thr Leu Cys Asp Ile Ser His Phe Phe Gln Glu Asp Asp Glu Thr Glu
                85                  90                  95

Ala Glu Pro Leu Leu Phe Arg Ala Val Pro Glu Cys Gln Leu Ser Gly
            100                 105                 110

Gly Asp Ile Pro Ser Val Ser Glu Glu Gln Glu Ser Ser Glu Gly Gln
            115                 120                 125

Asp Ser Gly Asp Ile Cys Ser Glu Glu Asn Gln Ile Val Ser Ser Tyr
        130                 135                 140

Ala Ser Lys Val Cys Phe Glu Ile Glu Glu Asp Tyr Lys Asn Arg Gln
145                 150                 155                 160

Phe Leu Gly Pro Glu Gly Asn Val Asp Val Glu Leu Ile Asp Lys Ser
            165                 170                 175

Thr Asn Arg Tyr Ser Val Trp Phe Pro Thr Ala Gly Trp Tyr Leu Trp
            180                 185                 190

Ser Ala Thr Gly Leu Gly Phe Leu Val Arg Asp Glu Val Thr Val Thr
            195                 200                 205

Ile Ala Phe Gly Ser Trp Ser Gln His Leu Ala Leu Asp Leu Gln His
        210                 215                 220
```

```
His Glu Gln Trp Leu Val Gly Gly Pro Leu Phe Asp Val Thr Ala Glu
225                 230                 235                 240

Pro Glu Glu Ala Val Ala Glu Ile His Leu Pro His Phe Ile Ser Leu
                245                 250                 255

Gln Ala Gly Glu Val Asp Val Ser Trp Phe Leu Val Ala His Phe Lys
                260                 265                 270

Asn Glu Gly Met Val Leu Glu His Pro Ala Arg Val Glu Pro Phe Tyr
                275                 280                 285

Ala Val Leu Glu Ser Pro Ser Phe Ser Leu Met Gly Ile Leu Leu Arg
                290                 295                 300

Ile Ala Ser Gly Thr Arg Leu Ser Ile Pro Ile Thr Ser Asn Thr Leu
305                 310                 315                 320

Ile Tyr Tyr His Pro His Pro Glu Asp Ile Lys Phe His Leu Tyr Leu
                325                 330                 335

Val Pro Ser Asp Ala Leu Leu Thr Lys Ala Ile Asp Asp Glu Glu Asp
                340                 345                 350

Arg Phe His Gly Val Arg Leu Gln Thr Ser Pro Pro Met Glu Pro Leu
                355                 360                 365

Asn Phe Gly Ser Ser Tyr Ile Val Ser Asn Ser Ala Asn Leu Lys Val
                370                 375                 380

Met Pro Lys Glu Leu Lys Leu Ser Tyr Arg Ser Pro Gly Glu Ile Gln
385                 390                 395                 400

His Phe Ser Lys Phe Tyr Ala Gly Gln Met Lys Glu Pro Ile Gln Leu
                405                 410                 415

Glu Ile Thr Glu Lys Arg His Gly Thr Leu Val Trp Asp Thr Glu Val
                420                 425                 430

Lys Pro Val Asp Leu Gln Leu Val Ala Ala Ser Ala Pro Pro Pro Phe
                435                 440                 445

Ser Gly Ala Ala Phe Val Lys Glu Asn His Arg Gln Leu Gln Ala Arg
                450                 455                 460

Met Gly Asp Leu Lys Gly Val Leu Asp Asp Leu Gln Asp Asn Glu Val
465                 470                 475                 480

Leu Thr Glu Asn Glu Lys Glu Leu Val Glu Gln Glu Lys Thr Arg Gln
                485                 490                 495

Ser Lys Asn Glu Ala Leu Leu Ser Met Val Glu Lys Lys Gly Asp Leu
                500                 505                 510

Ala Leu Asp Val Leu Phe Arg Ser Ile Ser Glu Arg Asp Pro Tyr Leu
                515                 520                 525

Val Ser Tyr Leu Arg Gln Gln Asn Leu
530                 535
```

```
<210> SEQ ID NO 12
<211> LENGTH: 159
<212> TYPE: PRT
<213> ORGANISM: Homo sapiens

<400> SEQUENCE: 12
```

```
Met Thr Gln Pro Thr Arg Pro Ser Val Thr Cys Asp Gln Gly Ser Ser
1               5                   10                  15

Thr Ile Gly Gly Thr Ala Ala Gln Ala Thr Thr Ser Ser Ser Ala Thr
                20                  25                  30

Ser Gly Ser Asn Tyr Gln Arg Asp Arg Leu Gly Arg Arg Pro Glu Ile
            35                  40                  45

Gly Val Gly Gly Gln Pro Gln Ile Cys Phe Pro Arg Pro Arg Ser Ala
```

-continued

```
    50                  55                  60

Gln Gln Pro Val Leu Phe Ser Leu Met Asn Ser Ser Glu Ala Ala Met
65                  70                  75                  80

Lys Lys Thr Leu Pro Lys Ser His Leu Ser Arg Val Ile Ile His Asp
                85                  90                  95

Asn Arg Ile Thr Gln Arg Ile Tyr Glu Met Glu Val Ser Ala Leu Glu
            100                 105                 110

Lys Thr Lys Lys Lys Ile Ser His Tyr Tyr Glu His Leu Lys Lys Lys
        115                 120                 125

Phe Met Thr Glu Gln Leu Arg Lys Leu Gly Arg Trp Arg Glu Glu Ser
    130                 135                 140

Val Asn Ser Asn Arg Tyr Leu Thr Phe Gly Ile Pro Pro Pro Val
145                 150                 155
```